US012635849B2

(12) United States Patent
Nielsen

(10) Patent No.: US 12,635,849 B2
(45) Date of Patent: May 26, 2026

(54) AUXILIARY COMPONENT WITH MEMORY FOR A MEDICAL VISUALISATION DEVICE

(71) Applicant: AMBU A/S, Ballerup (DK)

(72) Inventor: Brian Nielsen, Næstved (DK)

(73) Assignee: AMBU A/S, Ballerup (DK)

( * ) Notice: Subject to any disclaimer, the term of this patent is extended or adjusted under 35 U.S.C. 154(b) by 459 days.

(21) Appl. No.: 18/276,866

(22) PCT Filed: Mar. 1, 2022

(86) PCT No.: PCT/EP2022/055134
§ 371 (c)(1),
(2) Date: Aug. 10, 2023

(87) PCT Pub. No.: WO2022/184703
PCT Pub. Date: Sep. 9, 2022

(65) Prior Publication Data
US 2024/0122445 A1 Apr. 18, 2024

(30) Foreign Application Priority Data

Mar. 5, 2021 (DK) ............................ PA2021 70099

(51) Int. Cl.
*A61B 1/00* (2006.01)
*A61B 1/045* (2006.01)
(Continued)

(52) U.S. Cl.
CPC ...... *A61B 1/00016* (2013.01); *A61B 1/00009* (2013.01); *A61B 1/0002* (2013.01);
(Continued)

(58) Field of Classification Search
None
See application file for complete search history.

(56) References Cited

U.S. PATENT DOCUMENTS 4,646,721 A 3/1987 Arakawa
5,450,293 A 9/1995 Hoffman
(Continued)

FOREIGN PATENT DOCUMENTS

CN 103188987 A 7/2013
EP 1827258 B1 10/2011
(Continued)

OTHER PUBLICATIONS

Corrected International Search Report received for PCT/EP2022/ 055134, mailed Jul. 26, 2022, 5 pages., Jul. 26, 2022.
(Continued)

*Primary Examiner* — John P Leubecker
(74) *Attorney, Agent, or Firm* — Faegre Drinker Biddle & Reath LLP

(57) ABSTRACT
A medical visualisation system including a medical visualisation device for performing a medical visualisation procedure and a monitor device. The medical visualisation system includes an auxiliary component including an auxiliary memory and an auxiliary communication interface. The auxiliary memory storing initial data and the auxiliary component being configured to transmit the initial data to the monitor device using the auxiliary communication interface, and wherein a monitor processing unit of the monitor device is configured to receive the initial data and adjust one or more parameters of the medical visualisation system based on the initial data.

21 Claims, 10 Drawing Sheets

(51) Int. Cl.
    *A61B 1/06*         (2006.01)
    *A61B 1/267*       (2006.01)

(52) U.S. Cl.
    CPC .......... *A61B 1/0004* (2022.02); *A61B 1/0005*
        (2013.01); *A61B 1/00124* (2013.01); *A61B*
        *1/045* (2013.01); *A61B 1/00066* (2013.01);
        *A61B 1/00144* (2013.01); *A61B 1/0661*
        (2013.01); *A61B 1/267* (2013.01)

(56) References Cited

U.S. PATENT DOCUMENTS

| | | | |
|---|---|---|---|
| 5,940,126 A | | 8/1999 | Kimura |
| 6,106,457 A | * | 8/2000 | Perkins .............. A61B 1/00105 |
| | | | 600/172 |
| 6,796,939 B1 | | 9/2004 | Hirata et al. |
| 7,520,853 B2 | | 4/2009 | Amling et al. |
| 7,753,842 B2 | | 7/2010 | Glukhovsky et al. |
| 8,194,121 B2 | | 6/2012 | Blumzvig et al. |
| 8,194,122 B2 | | 6/2012 | Amling et al. |
| 8,465,421 B2 | | 6/2013 | Finkman et al. |
| 8,599,250 B2 | | 12/2013 | Amling et al. |
| 8,723,936 B2 | | 5/2014 | Amling et al. |
| 9,007,450 B2 | | 4/2015 | Amling et al. |
| 9,030,544 B2 | | 5/2015 | Tashiro et al. |
| 9,033,870 B2 | | 5/2015 | Farr et al. |
| 9,179,831 B2 | | 11/2015 | Mcgrail et al. |
| 9,386,914 B2 | | 7/2016 | Birnkrant et al. |
| 9,861,334 B2 | | 1/2018 | Tajima et al. |
| 11,265,450 B2 | | 3/2022 | Katsuki |
| 2003/0195390 A1 | | 10/2003 | Graumann |
| 2003/0228553 A1 | | 12/2003 | Mandelkern et al. |
| 2004/0243448 A1 | * | 12/2004 | Shoji ...................... G16H 30/20 |
| | | | 705/3 |
| 2006/0116667 A1 | | 6/2006 | Hamel et al. |
| 2007/0162095 A1 | * | 7/2007 | Kimmel ................. A61B 1/042 |
| | | | 600/172 |
| 2007/0195539 A1 | | 8/2007 | Dashiell |
| 2008/0139881 A1 | * | 6/2008 | Cover .................... H04N 7/185 |
| | | | 600/103 |
| 2008/0214896 A1 | | 9/2008 | Krupa et al. |
| 2009/0076331 A1 | | 3/2009 | Konwitz et al. |
| 2009/0247824 A1 | * | 10/2009 | Kawasaki ................ H04N 7/18 |
| | | | 600/109 |
| 2009/0270679 A1 | * | 10/2009 | Hoeg ................. A61B 1/00029 |
| | | | 600/109 |
| 2009/0318758 A1 | | 12/2009 | Farr et al. |
| 2010/0014174 A1 | | 1/2010 | Togino |
| 2010/0097453 A1 | * | 4/2010 | Endo ................. A61B 1/00016 |
| | | | 348/E7.085 |
| 2010/0141744 A1 | | 6/2010 | Amling et al. |
| 2010/0208054 A1 | | 8/2010 | Farr |
| 2011/0222746 A1 | | 9/2011 | Kotula et al. |
| 2011/0243116 A1 | | 10/2011 | Endo et al. |
| 2012/0134410 A1 | | 5/2012 | Kawasaki et al. |
| 2012/0162472 A1 | | 6/2012 | Amling et al. |
| 2012/0209071 A1 | | 8/2012 | Bayer et al. |
| 2012/0246374 A1 | | 9/2012 | Fino |
| 2012/0289858 A1 | | 11/2012 | Ouyang et al. |
| 2013/0092173 A1 | | 4/2013 | Alexander et al. |
| 2013/0103907 A1 | | 4/2013 | Katori et al. |
| 2013/0204085 A1 | | 8/2013 | Alexander et al. |
| 2014/0135576 A1 | | 5/2014 | Hebert |
| 2014/0275763 A1 | | 9/2014 | King et al. |
| 2015/0035967 A1 | | 2/2015 | Wodnicki et al. |
| 2015/0293877 A1 | * | 10/2015 | Liang ................. A61B 1/00016 |
| | | | 710/33 |
| 2016/0000300 A1 | | 1/2016 | Williams |
| 2016/0048536 A1 | | 2/2016 | Di et al. |
| 2016/0066770 A1 | | 3/2016 | Barbato et al. |
| 2016/0073855 A1 | | 3/2016 | Farr et al. |
| 2016/0213236 A1 | | 7/2016 | Hruska et al. |
| 2016/0299629 A1 | | 10/2016 | Doyle et al. |
| 2016/0344992 A1 | | 11/2016 | D'Alfonso et al. |

| | | | |
|---|---|---|---|
| 2017/0095297 A1 | | 4/2017 | Richmond et al. |
| 2017/0209027 A1 | | 7/2017 | Raj et al. |
| 2017/0280988 A1 | | 10/2017 | Barbato et al. |
| 2017/0311777 A1 | | 11/2017 | Hirayama et al. |
| 2018/0084986 A1 | | 3/2018 | Ochi et al. |
| 2018/0220873 A1 | * | 8/2018 | Tani ................... A61B 1/00036 |
| 2018/0296067 A1 | | 10/2018 | Amling et al. |
| 2018/0296289 A1 | | 10/2018 | Rodriguez-Navarro et al. |
| 2019/0052560 A1 | | 2/2019 | Smith |
| 2019/0104922 A1 | * | 4/2019 | Kasumi .............. A61B 1/00029 |
| 2019/0133430 A1 | | 5/2019 | Inglis et al. |
| 2019/0142256 A1 | | 5/2019 | Zhao et al. |
| 2019/0200844 A1 | | 7/2019 | Shelton et al. |
| 2019/0238791 A1 | | 8/2019 | Ingle |
| 2019/0261844 A1 | | 8/2019 | Walker et al. |
| 2019/0313881 A1 | | 10/2019 | Francher |
| 2019/0320879 A1 | | 10/2019 | Langell et al. |
| 2019/0335987 A1 | | 11/2019 | Cook |
| 2019/0350438 A1 | * | 11/2019 | Masuno ................. G02B 23/24 |
| 2020/0113412 A1 | | 4/2020 | Jensen |
| 2020/0273575 A1 | * | 8/2020 | Wolf ...................... B25J 9/1661 |
| 2020/0287899 A1 | | 9/2020 | Koizumi et al. |
| 2020/0305684 A1 | | 10/2020 | Hagihara |
| 2020/0405124 A1 | | 12/2020 | Sonnenborg et al. |
| 2021/0105467 A1 | * | 4/2021 | Tani ....................... H04N 7/183 |
| 2021/0113059 A1 | * | 4/2021 | Kasumi .............. A61B 1/00016 |
| 2021/0259522 A1 | | 8/2021 | Ubbesen et al. |
| 2021/0266435 A1 | | 8/2021 | Katsuki |
| 2021/0338040 A1 | | 11/2021 | Michihata et al. |
| 2022/0039634 A1 | | 2/2022 | Williams |
| 2022/0104822 A1 | | 4/2022 | Shelton et al. |
| 2022/0230643 A1 | | 7/2022 | Pai et al. |
| 2023/0037178 A1 | | 2/2023 | Kamon |
| 2024/0108207 A1 | * | 4/2024 | Yazdi ..................... A61B 1/267 |

FOREIGN PATENT DOCUMENTS

| | | | |
|---|---|---|---|
| EP | 2445210 A1 | 4/2012 |
| EP | 2286718 B1 | 12/2013 |
| EP | 2778999 A2 | 9/2014 |
| EP | 3417758 A1 | 12/2018 |
| EP | 3636133 A1 | 4/2020 |
| JP | 4918599 B2 | 4/2012 |
| JP | 2012-090974 A | 5/2012 |
| WO | 2008/063565 A2 | 5/2008 |
| WO | 2015/163942 A1 | 10/2015 |
| WO | 2019/198364 A1 | 10/2019 |
| WO | 2019/211938 A1 | 11/2019 |
| WO | 2020/031717 A1 | 2/2020 |
| WO | 2020/039716 A1 | 2/2020 |

OTHER PUBLICATIONS

Examination and Search Report for Denmark Application No. DK PA202170102, mailed on Jun. 21, 2021, 9 pages.

Examination and Search Report for Denmark Application No. PA202170098, mailed on May 18, 2021, 12 pages.

Examination and Search Report for Denmark Application No. PA202170099, mailed on Jun. 25, 2021, 8 pages.

Examination and Search Report for Denmark Application No. PA202170100, mailed on Jun. 25, 2021, 8 pages.

Examination and Search Report for Denmark Application No. PA202170101, mailed on Jun. 21, 2021, 9 pages.

International Search Report and Written Opinion received for PCT Patent Application No. PCT/EP2022/055139, mailed on Jun. 22, 2022, 14 pages.

International Search Report and Written Opinion received for PCT Patent Application No. PCT/EP2022/055133, mailed on Jun. 3, 2022, 10 pages.

International Search Report and Written Opinion received for PCT Patent Application No. PCT/EP2022/055134, mailed on Jul. 26, 2022, 14 pages.

International Search Report and Written Opinion received for PCT Patent Application No. PCT/EP2022/055135, mailed on Jun. 22, 2022, 9 pages.

(56)          References Cited

OTHER PUBLICATIONS

International Search Report and Written Opinion received for PCT Patent Application No. PCT/EP2022/055136, mailed on Aug. 5, 2022, 17 pages.

Office Action in related U.S. Appl. No. 18/240,847 dated May 30, 2025, 28 pages.

Office Action in related U.S. Appl. No. 18/276,861 dated Aug. 1, 2025, 27 pages.

Office Action in related U.S. Appl. No. 18/276,868 dated Aug. 4, 2025, 15 pages.

Office Action in related U.S. Appl. No. 18/276,868 dated Feb. 20, 2026, 22 pages.

Office Action in related U.S. Appl. No. 18/277,303 dated Aug. 27, 2025, 32 pages.

Office Action in related U.S. Appl. No. 18/277,303 dated Mar. 11, 2026, 30 pages.

Office Action in related U.S. Appl. No. 18/277,312 dated Dec. 17, 2025, 31 pages.

* cited by examiner

510

AUXILIARY COMPONENT WITH MEMORY FOR A MEDICAL VISUALISATION DEVICE

CROSS REFERENCE TO RELATED APPLICATIONS

This application is a National Phase entry under 35 U.S.C. § 371 of International Application No. PCT/EP2022/055134, filed Mar. 1, 2022, which claims the benefit of and priority from Danish Patent Application No. PA 2021 70099, filed Mar. 5, 2021. The foregoing applications are incorporated by reference herein in their entirety.

TECHNICAL FIELD

The present disclosure relates to a medical visualisation system and elements thereof. Particularly a medical visualisation system comprising an auxiliary component for a medical visualisation device, wherein data may be stored on the auxiliary component.

BACKGROUND

Wireless medical devices that utilize wireless communication from a medical device to a processing device is known in the art.

However, these technical solutions are not widespread as commercially available products, and particularly they are not widespread when it comes to single use products. There exists a vast spectrum of technical solutions providing a wireless communication link, but few fulfil the needs for medical devices at hospital settings.

For instance, not all communication frequencies may be used at hospitals and for medical devices, and in particular visualisation devices, such as endoscopes, very low latency is an important parameter. Moreover, usability and cost are driving factors defining suitable technical solutions.

SUMMARY

The present disclosure relates to a visualisation device, such as an endoscope, and a visualisation system, such as an endoscope system. Particularly, but not exclusively the visualisation device may be a disposable camera endoscope. Alternatively, the visualisation device may be a video laryngoscope. The visualisation system may further comprise a monitor device for being connected to the visualisation device, e.g. the monitor device may be configured to receive image data from the visualisation device.

It is an object of the present disclosure to provide a solution which at least improve the solutions of the prior art. Particularly, it is an object of the present disclosure to provide a medical visualisation system and components thereof to enhance flexibility and usability of the system. For example, the present disclosure provides solutions for enabling wireless transmission of video data from a medical visualisation device, such as an endoscope or a laryngoscope, to a monitor device or other suitable equipment.

Accordingly, a medical visualisation system and elements thereof are disclosed. The medical visualisation system may comprise one or more or all of the elements disclosed in the following.

A medical visualisation device is disclosed. The medical visualisation system may comprise the medical visualisation device. The medical visualisation device may completely or partly be a single-use product. The medical visualisation device may be an endoscope. For example, the medical visualisation device may comprise a handle and an insertion tube extending from the handle to a distal tube portion. The handle may comprise a control button adapted to receive an input in a first input direction and/or in a second input direction. The touch input in the first input direction may cause a bendable section of the insertion tube to bend in a first bending direction. The touch input in the second input direction may cause the bendable section to bend in a second bending direction. Other examples of the medical visualisation device may be a laryngoscope or an endotracheal tube with integrated camera.

The medical visualisation device comprises an image sensor adapted to generate image data indicative of a view from the medical visualisation device and a light emitter adapted to provide illumination of the view. The view may be a view from the distal tube portion of the insertion tube. The light emitter may be an LED, an optical fibre, or similar element known to provide illumination. The medical visualisation device further comprises a device processing unit adapted to receive the image data from the image sensor and optionally encode the image data to provide encoded image data based on the image data. The device processing unit may comprise an image signal processor (ISP), a complex programmable logic device (CPLD), a field-programmable gate array (FPGA) and/or other suitable processing unit elements. The device processing unit may comprise memory, such as buffer memory.

The medical visualisation device comprises a device communication interface. For example, the medical visualisation device may comprise a device wireless communication module adapted to communicate with a monitor wireless communication module of a monitor device, such as the monitor device also disclosed herein. The device wireless communication module may be connected to the device processing unit. The device wireless communication module is adapted to receive the image data and/or the encoded image data from the device processing unit and transmit the image data and/or the encoded image data using a downstream data channel to the monitor wireless communication module.

Also disclosed is an auxiliary component. The medical visualisation system may comprise the auxiliary component. The auxiliary component may be couplable to a main device part to form the disclosed medical visualisation device, wherein the main device part comprises the image sensor and the light emitter and a main coupling part. The main device part may further comprise the handle and/or the insertion tube, as described above.

The auxiliary component may be couplable to the main device part. The auxiliary component comprises an auxiliary coupling part adapted to couple with the main coupling part. The auxiliary component further may comprise the device processing unit. The auxiliary component may further comprise one or more auxiliary communication interfaces. For example, the auxiliary component may comprise the device wireless communication module.

The main device part may be a single-use product. The auxiliary component may be a re-usable product. Hence, the auxiliary component may be adapted to be coupled to a plurality of main device parts.

The auxiliary component or part thereof may be a dongle for insertion into a designated receiver of the main device part. Alternatively or additionally, the auxiliary component or part thereof may be a wearable device, such as a wrist-watch or an armband.

Also disclosed is a monitor device. The medical visualisation system may comprise the monitor device. The monitor device is operable to receive image data from a medical visualisation device, such as the disclosed medical visualisation device. The monitor device comprises a first housing. The medical visualisation system may comprise a display. The monitor device may comprise the display, e.g. accommodated in the first housing or couplable to the first housing, e.g. the display may be supported by the first housing or affixed to the first housing. Alternatively, the monitor device, such as the first housing, may be couplable to the display, e.g. the display may be an external display. For example, the monitor device may be devoid of a display. The display, whether forming part of the monitor device or not, may be a touch sensitive display.

The monitor device further comprises one or more monitor communication interfaces. For example, the monitor device may comprise a monitor wireless communication module adapted to communicate with a device wireless communication module of the medical visualisation device. The monitor wireless communication module may be adapted to receive image data and/or encoded image data using a downstream data channel from the device wireless communication module to the monitor wireless communication module.

The monitor device further comprises a monitor processing unit adapted to receive the image data and/or the encoded image data from the monitor wireless communication module, optionally decode the encoded image data, and cause the display to display a live representation of the image data. The monitor processing unit may comprise a complex programmable logic device (CPLD), a field-programmable gate array (FPGA) and/or other suitable processing unit elements. The monitor processing unit may comprise memory, such as buffer memory.

The monitor device may further comprise a monitor memory. The monitor memory may be connected to the monitor processing unit. The monitor processing unit may be adapted to read and/or write data from the monitor memory. The monitor memory may be any suitable electronic memory. The monitor memory may be non-volatile memory, such as a Flash memory.

The auxiliary component may comprise auxiliary memory. The auxiliary memory may be non-transitive memory. The auxiliary memory may store initial data, e.g. for being loaded by the monitor device. The initial data is preferably stored in the auxiliary memory prior to coupling the auxiliary component and the main device part, such as prior to coupling the auxiliary coupling part and the main coupling part. The initial data may be different than and/or unrelated to the image data. The initial data may be not generated by the image sensor. The auxiliary component may be configured to transmit and/or be enablable to transmit the initial data to the monitor device, e.g. using an auxiliary communication interface, such as the device wireless communication module or other suitable communication interfaces for transmitting the initial data to the monitor device. The monitor processing unit may be adapted to receive the initial data and adjust one or more parameters of the medical visualisation system based on the initial data.

The medical visualisation system may comprise a plurality of medical visualisation devices, e.g. comprising a first medical visualisation device and a second medical visualisation device, each of which may comprise some or all of the features as described in relation to the medical visualisation device disclosed herein. The plurality of medical visualisation devices may be different visualisation devices. In an example, the first medical visualisation device may be an endoscope comprising a flexible tube and the second medical visualisation device may be a video laryngoscope.

The plurality of medical visualisation devices may be different types, e.g. configured for different clinical purposes. For example, the first medical visualisation device may be a first device type configured for a first clinical purpose, and the second medical visualisation device may be a second device type configured for a second clinical purpose. An exemplary clinical purpose may be urology. For example, the first device type or the second device type may be a urology endoscope, such as a cystoscope or a ureteroscope. Another exemplary clinical purpose may be gastroenterology. For example, the first device type or the second device type may be a gastro-intestinal endoscope, such as a gastroscope, a duodenoscope or a colonoscope. Yet another exemplary clinical purpose may be pulmonology. For example, the first device type or the second device type may be a pulmonology endoscope, such as a bronchoscope.

The plurality of medical visualisation devices may comprise image sensors of same or different image sensor type. For example, the image sensor of the first medical visualisation device may be a first image sensor type and the image sensor of the second medical visualisation device may be a second image sensor type. Alternatively, the image sensor of the second medical visualisation device may be the first image sensor type. Alternatively or additionally, the image sensor of a third medical visualisation device may be a third image sensor type or the second image sensor type. The image sensor types may differ on various aspects, e.g. by power supply voltage, by image resolution, by physical size etc.

The auxiliary component may be couplable to the plurality of medical visualisation devices, e.g. the auxiliary component may be couplable both to the first medical visualisation device and the second medical visualisation device and/or the third medical visualisation device. Hence, for example, one auxiliary component may be couplable to a range of different medical visualisation devices.

It is an advantage of the present disclosure that, e.g. in addition to facilitating wireless transfer of image data from the image sensor, the auxiliary component may ease setup of the system prior to a procedure and/or may be used to contain data obtained from the procedure.

It is a further advantage of the present disclosure that operators may use equipment of other departments (e.g. where conventional setup may be different) in a familiar way.

BRIEF DESCRIPTION OF THE FIGURES

Embodiments of the disclosure will be described in more detail in the following with regard to the accompanying figures. The figures show one way of implementing the present disclosure and are not to be construed as being limiting to other possible embodiments falling within the scope of the attached claim set.

DETAILED DESCRIPTION

Figure 1A:
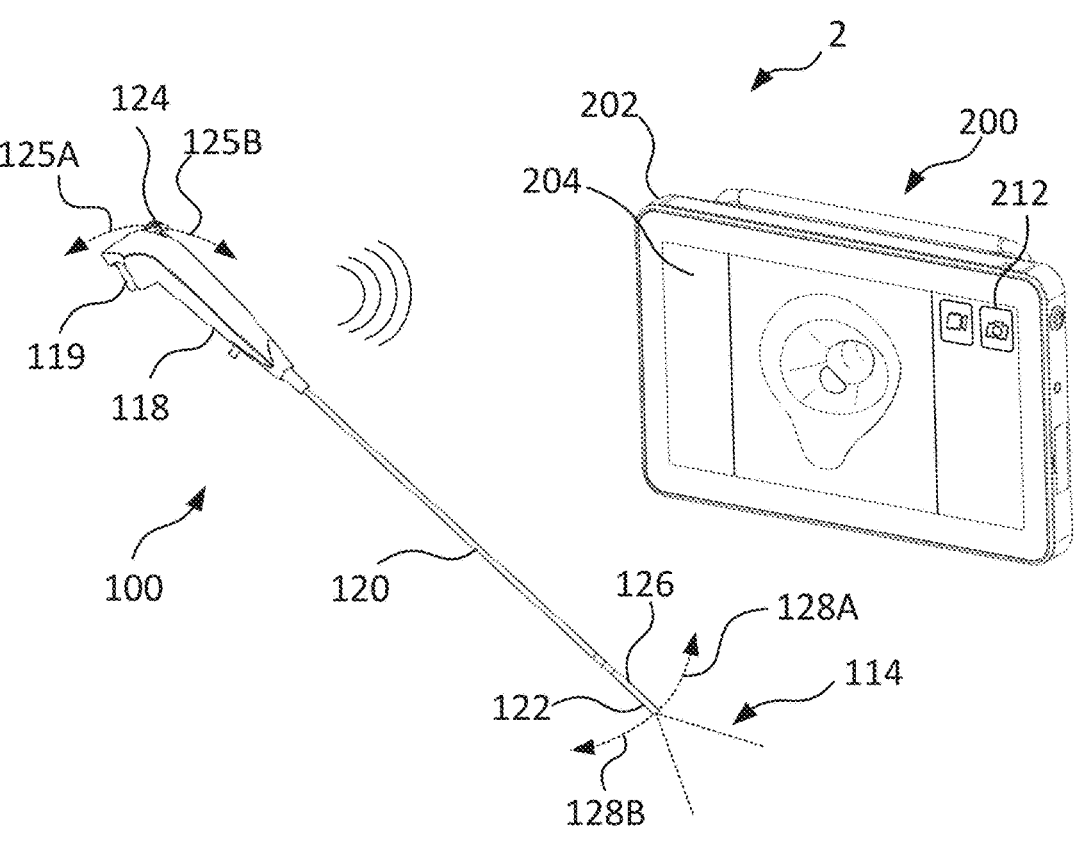
FIGS. 1A and 1B schematically illustrates an exemplary medical visualisation system, FIG. 2 schematically illustrates an exemplary medical visualisation device, FIGS. 3A and 3B schematically illustrate the medical visualisation device.

Further details of the aspects of the disclosure, as set out above, are provided in the following. Details and/or advantages may be practiced in any embodiment and/or aspect even if not so illustrated, or if not so explicitly described.

The main part of the medical visualisation device and the auxiliary component may be couplable by a main coupling part of the main part and an auxiliary coupling part of the auxiliary component. The auxiliary coupling part may be adapted to couple with the main coupling part. The main coupling part may be adapted to couple with the auxiliary coupling part. The main coupling part may have one or more main terminals electrically connected to the light emitter and image sensor. The auxiliary coupling part may comprise one or more auxiliary terminals adapted to connect to the one or more main terminals, e.g. when the auxiliary coupling part is coupled with the main coupling part.

The device processing unit may be electrically connected to the one or more auxiliary terminals and may be adapted to receive the image data from the image sensor, e.g. via the one or more auxiliary terminals, e.g. when the auxiliary component is coupled to the main device part, such as when the auxiliary coupling part is coupled with the main coupling part.

The auxiliary component may comprise a battery, such as a rechargeable battery, e.g. a Li-Ion battery or another suitable battery. The battery may be adapted to power the device processing unit and/or the device wireless communication module. The battery may be electrically connected to the device processing unit and/or the device wireless communication module, such as to power the device processing unit and/or the device wireless communication module. The battery may be electrically connected to the one or more auxiliary terminals. The battery may be adapted to power the image sensor and light emitter of the main device part, e.g. via the one or more auxiliary terminals, e.g. when the auxiliary component is coupled to the main device part, such as when the auxiliary coupling part is coupled with the main coupling part. The battery may, when fully charged, comprise a battery capacity allowing at least 2 hours of continued usage of the medical visualisation device.

The auxiliary component may comprise a battery indicator indicative of remaining capacity of the battery. The battery indicator may be an LED or other suitable means for providing an indication of remaining battery capacity. Thus, an operator of the medical visualisation device may be alerted if battery capacity is running low. The battery indicator may comprise a plurality of bars (e.g. five) indicative of capacity of the battery, e.g. fewer bars displayed for less battery capacity. Alternatively or additionally, the battery indicator may indicate battery capacity by being lit in different colours, e.g. green (indicative of full or near full charge), yellow (medium capacity), red (low capacity). Bars and colour may be combined. For example, by the five following levels of indication, from full capacity to near empty: Five bars and green, four bars and green, three bars and yellow, two bars and yellow, one bar and red. The battery indicator may be flashing, e.g. red, when the battery capacity is below a threshold capacity.

The battery indicator may be adapted to receive a user input, e.g. a touch input, and in response to the user input, the battery indicator may provide a signal indicative of battery capacity. For example, an LED indicator may light up in a colour, e.g. green/yellow/red, indicative of estimated battery capacity.

The auxiliary component may comprise an auxiliary housing. The auxiliary housing may enclose elements of the auxiliary component, such as the device processing unit and/or the 1156R device wireless communication module and/or the battery. The auxiliary housing may be fluid-tight to the outside, e.g. such that the auxiliary component is adapted for wet cleaning, e.g. by immersion in a liquid. For example, the auxiliary housing may be surface coated with a sealing liquid, e.g. by immersion in the sealing liquid, to make the auxiliary housing fluid-tight to the outside. Alternatively or additionally, the terminals of the auxiliary component may be provided by insert moulding, whereby the conductive terminals may be provided, during moulding, in respective positions in the mould for moulding, e.g. by injection moulding, the auxiliary housing. The auxiliary housing may be IP67 compliant.

The main device part, such as the main coupling part of the main device part, may comprise a safety-circuit. The safety circuit may be adapted to prevent excessive current to elements of the main device part, such as the light emitter and/or image sensor. For example, the one or more main terminals may be electrically connected to the elements of the main device part, such as the light emitter and/or the image sensor, via the safety circuit.

The main device part, such as the main coupling part of the main device part, may comprise a device identifier comprising device identifier information, e.g. to allow identification of the main device part, e.g. including serial number, batch number, device type, etc. The device processing unit may be adapted to obtain the device identifier information from the device identifier. The device processing unit and/or the monitor processing unit may be adapted to configure the auxiliary component and/or the monitor device to be configured according to the obtained device identifier information, e.g. such as to be compatible with the main device part.

The device identifier may include an electronically readable memory, such as an EPROM, RFID, NFC or similar. In other examples the device identifier may be a QR-code, bar-code or similar. The device identifier, or the electronically readable memory of the device identifier, may be connected to the one or more main terminals. Alternatively, the device identifier may be readable without the necessity to establish an electrical contact. For example, the device identifier may be readable by means of a short-range communication circuit, such as an RFID or NFC circuit.

Providing the main device part with a safety circuit and/or a device identifier facilitates that the auxiliary component may be used with different disposable parts, e.g. gastroscopes, bronchoscopes, laryngoscopes etc.

The device wireless communication module and/or the monitor wireless communication module may be adapted to communicate wirelessly, such as to wirelessly receive and/or wirelessly transmit data, e.g. image data, encoded image data and/or other data described herein. The device wireless communication module and/or the monitor wireless communication module may be adapted to communicate using a radio frequency of more than 10 GHZ, such as using a radio frequency between 57-66 GHZ, such as between 57-64 GHZ, such as between 57.05-64 GHZ, such as between 59-64 GHZ, such as between 59.4-63.56, such as between 59.4-62.9 GHZ. These frequencies facilitate high bandwidth and low latency for the live images to be displayed on the display. Furthermore, the exemplary frequencies have a limited range making it advantageous to use for medical visualisation procedures, as this lowers the risk of the image data being interceptable or interfering with other procedures outside the room wherein the procedure is being performed.

The wireless communication modules may comprise an antenna. For example, the monitor wireless communication module may comprise a monitor antenna, and/or the device wireless communication module may comprise a device antenna. The image data and/or the encoded image data from the device wireless communication module may be transmitted to the monitor wireless communication module via the device antenna and the monitor antenna. It may be advantageous to ensure or promote line of sight between the device antenna and the monitor antenna. Especially for wireless communication utilizing very high radio frequencies, e.g. above 10 GHz, such as between 57-66 GHZ, obstacles between transmitter and receiver have a high likelihood of influencing the data transfer.

The monitor antenna may be positioned external to a housing of the monitor device, such as the first housing. The monitor antenna may be positioned at a distance from the housing, e.g. of more than 2 meters, and/or the monitor antenna may be adapted to be positioned above an operating setting, such as at the ceiling of an operating room. The monitor antenna may be positioned above the first housing. The monitor antenna may be wired to a housing of the monitor device, such as the first housing. The device antenna may be positioned external to a housing of the auxiliary component, such as the auxiliary housing. The device antenna may be positioned at a distance from the auxiliary housing, e.g. of more than 0.5 meters. The device antenna may be adapted to be positioned near or at the head of the operator, or at an upper arm of the operator. Alternatively, the device antenna may form part of the housing. Alternatively, the device antenna may be enclosed in the auxiliary housing. The auxiliary housing may be formed to allow transmission therethrough of the wireless signal between the device wireless communication module and the monitor wireless communication module. The auxiliary housing may be provided as a wearable device, i.e. the auxiliary housing and/or the device antenna may, thereby, be worn by the operator in a position that promotes line of sight with the monitor antenna. The monitor antenna and the device antenna may be positioned with line of sight there between.

The auxiliary memory may store initial data, e.g. for being loaded by the monitor device. The auxiliary component may be configured to transmit and/or be enablable to transmit the initial data to the monitor device, e.g. using an auxiliary communication interface, such as the device wireless communication module or other suitable communication interfaces for transmitting the initial data to the monitor device. The monitor processing unit may be adapted to receive the initial data and adjust one or more parameters of the medical visualisation system based on the initial data.

The auxiliary component may be adapted for attachment to an operator of the medical visualisation system, such as to an arm of the operator or a head of the operator. The auxiliary component may comprise a wearing element, such as a strap, a clip or similar, to attach the auxiliary component to the operator. Particularly, when storing personalized information, it is advantageous to provide the auxiliary component as a wearable component.

The monitor device may comprise one or more monitor communication interfaces adapted to communicate with the auxiliary communication interface. The monitor processing unit may be adapted to receive the initial data via the monitor communication interface. For example, the one or more monitor communication interfaces may comprise the monitor wireless communication module or other suitable communication interfaces for receiving the initial data from the auxiliary component.

The initial data may comprise patient data, e.g. of the patient on which the procedure is about to be performed, such as patient name, social security number, medical history, information about allergies, etc. The monitor processing unit may be adapted to associate the patient data with the image data and/or any captured image data files or video sequence files. Thus, the auxiliary component may be adapted to follow the patient, and upon performing a procedure, data of the patient may be automatically received by the monitor device.

Alternatively or additionally, the initial data may comprise operator data, e.g. indicative of the operator performing the medical visualisation procedure, such as name, identification number, etc. The monitor processing unit may be adapted to associate the operator data with the image data and/or any captured image data files or video sequence files. Thus, the auxiliary component may be adapted to follow the operator, and upon performing a procedure, data of the operator may be automatically received by the monitor device. The operator data may alternatively or additionally be indicative of a username or other logon credentials of the operator, and the monitor processing unit may be adapted to initiate a logon procedure of the monitor device using the username or other logon credentials indicated by the initial data. Thereby, the user may more easily logon to the monitor device and/or an associated IT-system, e.g. by only providing a password or other authentication method, which may include contactless authentication methods, such as biometric recognition, such as facial recognition or similar. Hence the logon procedure may be faster as the username or other logon credentials need not be entered manually.

Alternatively or additionally, the initial data may comprise operator setup data, e.g. associated with the operator performing the medical visualisation procedure.

The operator setup data may include image parameters, e.g. including one or more of settings of hue, saturation, brightness, contrast, and sharpness. The monitor processing unit may, in response to receiving the initial data, adjusts image parameters of the live representation of the image data displayed on the display in accordance with the image parameters of the operator setup data. Thus, the system may conveniently adjust parameters to be in accordance with preferences of the operator, thereby reducing unnecessary time to setup the monitor device in accordance with individual preferences of an operator.

The medical visualisation system, such as the monitor device and/or the medical visualisation device may, as previously described, comprise one or more buttons adapted to receive user inputs. The operator setup data may include button settings indicative of functions assigned to one or more buttons of the medical visualisation system, e.g. on the handle of the main device part or on the monitor device. The monitor processing unit may, in response to receiving the initial data, assign functions to the one or more of the buttons in accordance with the button settings of the operator setup data. Thus, the system may conveniently setup the devices in accordance with preferences of the operator, thereby reducing unnecessary manual setup time prior to a procedure.

The monitor processing unit and/or the device processing unit may be adapted to perform tasks based on spoken inputs. For example, the monitor device may comprise a microphone, or a microphone may be coupled to the monitor device, adapted to register utterances from the operator. The operator setup data may include voice control data associated with the operator, e.g. including keywords, training data etc. The monitor processing unit, after receiving the initial data, may identify tasks to be performed based on the spoken inputs and the voice control data of the initial data.

The monitor processing unit may be adapted to store new operator setup data, and/or to update the currently stored operator setup data in the auxiliary memory based on a current set of settings of the monitor device. For example, the monitor processing unit may store or update operator setup data in the auxiliary memory in response to receipt of a user input signal indicative of a user requesting storing of the current set of settings. For example, a designated button may be provided, or a certain input, e.g. pressing a predetermined button for more than a predetermined time, may activate a storing/updating procedure of the operator setup data. Previous versions of the operator setup data may be accessible via a menu on the monitor device, such as to allow recovery of previous settings, in case new settings were stored in error or were not satisfactory.

The main coupling part and the auxiliary coupling part may have corresponding engagement members, for mechanically coupling the main coupling part and the auxiliary coupling part. The main coupling part may be engaging mechanical coupling with the auxiliary coupling part by displacing the main coupling part along an engagement direction. The main coupling part may be disengaging mechanical coupling with the auxiliary coupling part by displacing the main coupling part along a disengagement direction. The disengagement direction may be opposite the engagement direction. Alternatively, the disengagement direction may be perpendicular to the engagement direction.

The monitor device may comprise a component socket. The component socket may be adapted to engage with the auxiliary component. The component socket may be adapted to pair the monitor device and the auxiliary component, e.g. to pair the monitor wireless communication module and the device wireless communication module. The component socket may comprise one or more monitor terminals, e.g. exposed terminals. The one or more monitor terminals may be adapted to contact corresponding (e.g. exposed) terminals of the auxiliary component. The one or more monitor communication interfaces, for receiving the initial data from the auxiliary component, may comprise the component socket.

The auxiliary component may comprise a secondary auxiliary coupling part, e.g. in addition to the auxiliary coupling part already described. The secondary auxiliary coupling part may have one or more secondary auxiliary terminals, e.g. electrically connected to the device processing unit and/or the one or more auxiliary terminals of the auxiliary coupling part previously described. The one or more auxiliary communication interfaces, for transmitting the initial data to the monitor device, may comprise the auxiliary coupling part and/or the secondary auxiliary coupling part.

The monitor device may comprise a monitor coupling part. The monitor coupling part may be adapted to couple with the auxiliary coupling part and/or the secondary auxiliary coupling part. The monitor coupling part may facilitate a direct connection between the monitor device and the auxiliary component, thereby providing a backup solution in case wireless transmission between the auxiliary component and the monitor device is not working. Alternatively or additionally, the monitor coupling part may facilitate transmission of the initial data from the auxiliary component to the monitor device.

The monitor coupling part may comprise one or more monitor terminals. The one or more monitor terminals may be adapted to connect to the one or more auxiliary terminals and/or the one or more secondary auxiliary terminals. The monitor processing unit may be electrically connected to the one or more monitor terminals. The monitor processing unit may be adapted to, e.g. when the monitor coupling part is coupled with the secondary auxiliary coupling part, receive the image data and/or the encoded image data from the image sensor, e.g. via the monitor coupling part being coupled with the secondary auxiliary coupling part, and cause the display to display a live representation of the image data.

The monitor coupling part may comprise one or more flexible monitor wires. The monitor terminals may be arranged at a distal end of the one or more flexible monitor wires. A housing of the monitor device may be arranged at a proximal end of the one or more flexible monitor wires. Alternatively, a coupling plug for coupling with a coupling socket of the monitor device may be arranged at the proximal end of the one or more flexible monitor wires. Accordingly, the monitor device may comprise a coupling socket for receiving the coupling plug. The one or more monitor terminals may be electrically connected to the monitor processing unit through the one or more flexible monitor wires. One or more elements of the monitor coupling part, e.g. the one or more flexible monitor wires and/or the monitor terminals, may be enclosed in a sealed package. A coupling plug, as described above, may be coupled to the proximal end of the one or more flexible monitor wires and be arranged outside the sealed package.

The monitor processing unit may be adapted to perform an electronic analysis of the monitor coupling part, e.g. at predetermined intervals. In accordance with registering a non-working condition of the monitor coupling part or of elements of the monitor coupling part, the monitor processing unit may activate a warning indication to prompt the user to replace the monitor coupling part. This may be especially advantageous when the monitor coupling part comprises electronic components that may fail and in particular in examples where elements of the monitor coupling part is enclosed in a sealed package, e.g. for single use. For example, if the sealed devices are not properly working, the monitor device may prompt replacement of the electronic components.

The main device part may comprise one or more flexible device wires. The one or more flexible device wires may extend between the main coupling part and the handle of the main device part. The one or more main terminals may be electrically connected to the light emitter and the image sensor through the one or more flexible device wires. Providing flexible device wires as part of the main device part allows the auxiliary component to be positioned at a greater distance from the patient, e.g. on an upper arm of the operator, thereby decreasing the risk of contaminating the auxiliary component, which may be a reusable device.

The term "flexible" with respect to wires may mean that a user is able to bend the wires, without damaging the wires, such as to position the respective coupling parts appropriately for attachment.

Particularly, in examples where the main coupling part may be repositioned relative to the handle of the main device part, e.g. by being coupled with flexible device wires, electronic components of the main device part, such as the safety circuit and/or the device identifier, may advantageously be provided in the main coupling part, such as to lower the weight of the handle.

The one or more monitor communication interface may comprise exposed electrical terminals to contact corresponding exposed electrical terminals of the one or more auxiliary communication interface. For example, the one or more monitor communication interface may comprise the component socket and/or the monitor coupling element, which may comprise exposed electrical terminals. The one or more auxiliary communication interface may comprise the auxiliary coupling part and/or the secondary auxiliary coupling part, which may comprise corresponding exposed electrical terminals of the one or more auxiliary communication interface.

The one or more monitor communication interface may comprise a short-range communication circuit adapted to inductively communicate with a corresponding short range communication circuit of the one or more auxiliary communication interface. For example, the short-range communication circuits may be contactless, e.g. inductive, communication circuits, e.g. using near field communication (NFC) or another suitable short range communication technology.

The auxiliary component, such as the device processing unit, may be adapted to encode the initial data together with the image data in the encoded image data. Thus, the initial data may be transmitted to the monitor device embedded in the encoded image data.

Alternatively or additionally, the initial data may be transmitted to the monitor device during an initialisation procedure, e.g. before transmitting the image data/encoded image data to the monitor device. For example, the initial data may be transmitted to the monitor device in response to the operator holding the auxiliary component near a designated area on the monitor device, e.g. using short-range communication circuits. For example, the initial data may be transferred to the monitor device using the short-range communication circuits, when the short-range communication circuit of the auxiliary component is brought within an interrogating distance of the short-range communication circuit of the monitor device. Alternatively or additionally, the initial data may be transmitted to the monitor device in response to the operator connecting the auxiliary component, e.g. the auxiliary coupling part or the secondary auxiliary coupling part, to the monitor coupling part and/or the component socket of the monitor device. For example, the initial data may be transferred to the monitor device, when the exposed electrical terminals of the monitor device contact the corresponding exposed electrical terminals of the auxiliary component. After initially having transmitted the initial data to the monitor device, the operator may attach the auxiliary component to the main device part to begin wireless transmission of the image data/encoded image data to the monitor device.

Alternatively or additionally, the device wireless communication module may transmit the initial data to the monitor wireless communication module during the initialisation procedure before transmitting the image data/encoded image data. Hence, the initial data may be transmitted to the monitor device in response to establishing wireless connection between the device wireless communication module and the monitor wireless communication module, e.g. while the auxiliary component is coupled with the main device part.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1A schematically illustrates an exemplary medical visualisation system 2 comprising an exemplary medical visualisation device 100 and an exemplary monitor device 200. In the illustrated example, the medical visualisation device 100 is an endoscope, such as a bronchoscope. In other examples, the medical visualisation device og the medical visualisation system may be a laryngoscope, a gastro-intestinal endoscope, a urology endoscope, etc.

The medical visualisation device 100 comprises a handle 118, and, in the illustrated example, the medical visualisation device 100 comprises an insertion tube 120 extending from the handle 118 to a distal tube portion 122. The handle may, as illustrated, comprise a control button 124 and the insertion tube 120 may comprise a bendable section 126. The control button 124 is adapted to receive an input in a first input direction 125A and in a second input direction 126B. The bendable section 126 is adapted to bend accordingly in a first bending direction 128A and a second bending direction 128B. A touch input in the first input direction 125A causes the bendable section 126 to bend in the first bending direction 128A. A touch input in the second input direction 125B causes the bendable section 126 to bend in the second bending direction 128B.

The medical visualisation device 100 has an image sensor adapted to generate image data indicative of a view 114 from the visualisation device. As illustrated, the view 114 from the visualisation device 100 may be from the distal tube portion 122 of the insertion tube 120. The medical visualisation device 100 further comprises a light emitter adapted to provide illumination of the view 114.

The medical visualisation device 100 and the monitor device 200 are adapted to communicate wirelessly. For example, the medical visualisation device 100 is adapted to transmit image data using a downstream data channel from the medical visualisation device 100 to the monitor device 200.

Alternatively or additionally, the medical visualisation device may be adapted to receive settings data using an upstream data channel from the monitor device 200 to the medical visualisation device 100.

The monitor device 200 comprises a first housing 202. In the illustrated example, the monitor device 200 further comprises a display 204 accommodated in the first housing 202. In alternative examples, the monitor device 200, such as the first housing 202 of the monitor device 200, may be coupled to an external display (see FIG. 1B). The monitor device 200 is operable to receive image data from a medical visualisation device 100 and display on the display a live representation of the image data indicative of the view 114 from the visualisation device 100. The display 204 may be a touch sensitive display.

The monitor device 200 may be adapted to wirelessly communicate with the medical visualisation device 100. For example, the monitor device 200 may be adapted to receive image data using the downstream data channel from the medical visualisation device 100 to the monitor device 200. The monitor device 200 may further be adapted to transmit settings data using an upstream data channel from the monitor device 200 to the medical visualisation device 100. Such settings data may, for example, be used to adjust brightness of the light emitter or control colour, contrast, gain and/or exposure settings of the image sensor. These settings may be adaptively adjusted based on the received image data, e.g. to adjust under/over exposure or similar.

The medical visualisation system 2 may be operable to store an image data file and/or a video sequence file in response to receipt of a user input signal indicative of a user activating an image capture button 119, 212. The image capture button may be a device button 119 on the medical visualisation device 100, and/or a monitor button 212 on the monitor device 200, e.g. a soft button displayed on the display 204.

Figure 1B:
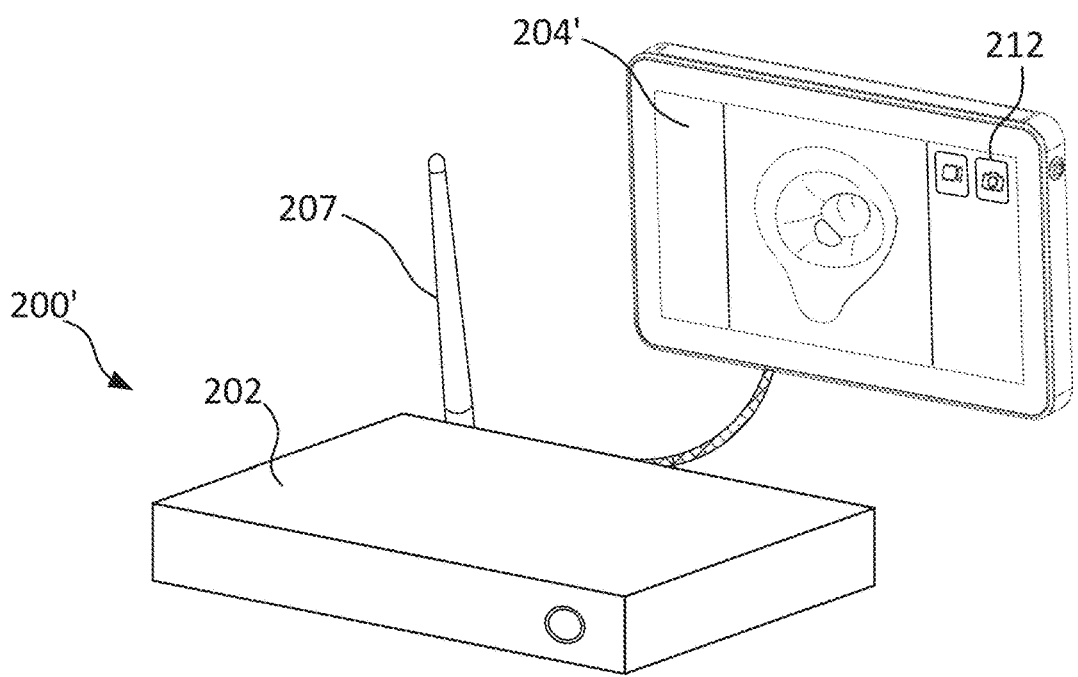

FIG. 1B schematically illustrates a monitor device 200' comprising a first housing 202, wherein the monitor device 200, such as the first housing 202, may be coupled to an external display 204'. The external display 204' may be a touch sensitive display. Other than the display 204' being external to the first housing 202, the monitor device 200' may be similar and comprise the same functionality as the monitor device 200. For example, the monitor device 200' is operable to receive image data from a medical visualisation device 100 (FIG. 1A) and display on the display 204' a live representation of the image data indicative of the view 114 from the visualisation device 100.

The monitor device 200' may be adapted to wirelessly communicate with the medical visualisation device 100. For example, the monitor device 200' may be adapted to receive image data using the downstream data channel from the medical visualisation device 100 to the monitor device 200'. The monitor device 200' may further be adapted to transmit settings data using an upstream data channel from the monitor device 200' to the medical visualisation device 100.

It is emphasized that the monitor device 200, as illustrated in the following examples may be substituted by the monitor device 200', as illustrated in FIG. 1B.

Figure 2:
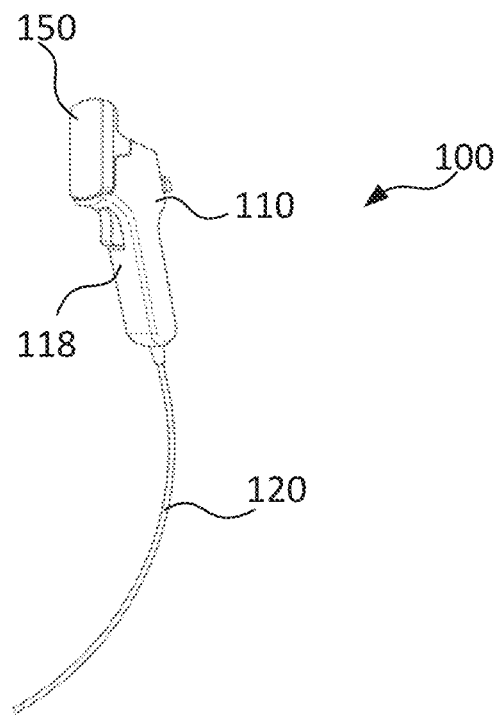

FIG. 2 schematically illustrates an exemplary medical visualisation device 100, such as the medical visualisation device 100 as described with respect to FIG. 1A.

The medical visualisation device 100 of FIG. 2 further comprises an auxiliary component 150 couplable to a main device part 110 of the medical visualisation device 100. The main device part 110 comprises the handle 118 and the insertion tube 120, as described with respect to FIG. 1A. The auxiliary component 150 comprises various electronic components, e.g. for establishing wireless communication with the monitor device.

The auxiliary component 150 may be adapted to be used multiple times, e.g. being reusable, while the man device part 110 may be configured as a single-use product, e.g. being disposable. By providing electronic components in a reusable component while the main device part being in direct contact with the patient being disposable, valuable resources may be preserved and costs may be lowered, while observing increased patient safety and reduced risk of cross contamination.

Figure 3A:
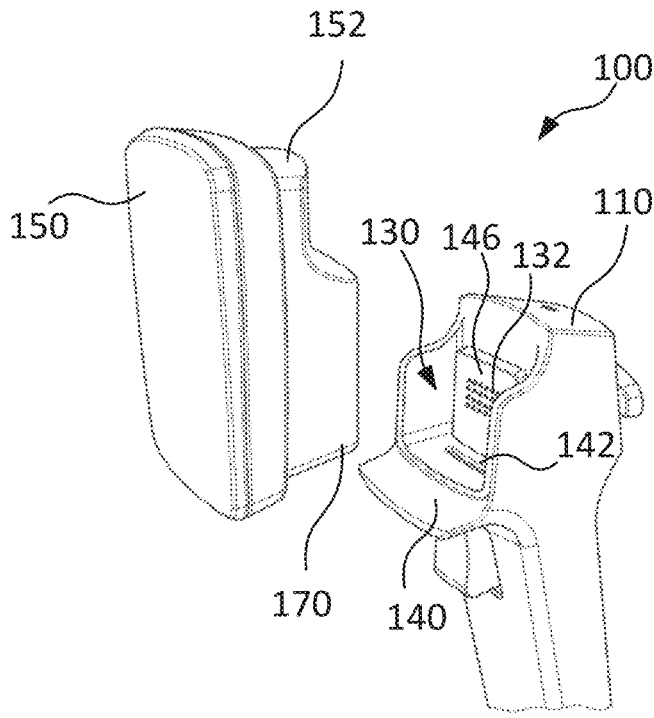
Figure 3B:
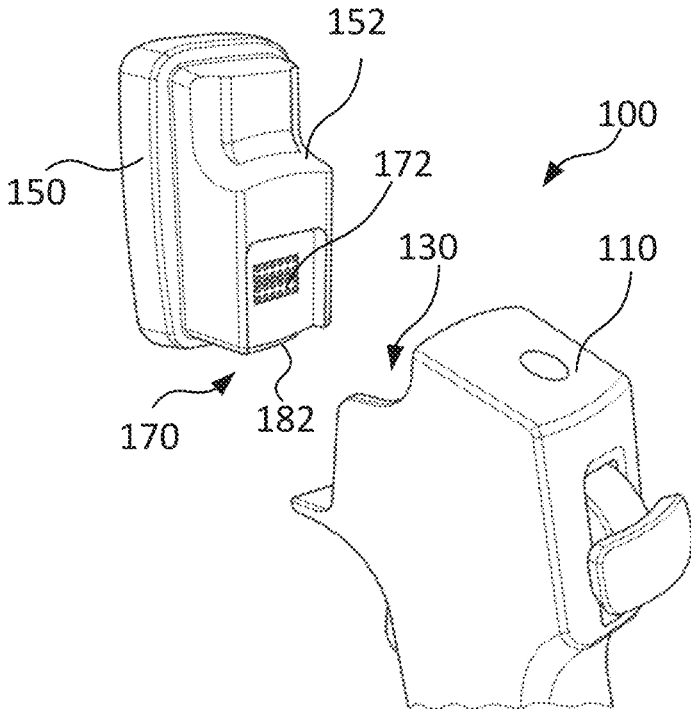

FIGS. 3A and 3B schematically illustrate the medical visualisation device 100, as also illustrated in FIG. 2, wherein the auxiliary component 150 is detached from the main device part 110.

The auxiliary component 150 comprises an auxiliary housing. The auxiliary housing 152 may be fluid-tight to the outside such that the auxiliary component 150 is adapted for wet cleaning, e.g. by immersion in a liquid. For example, the auxiliary housing 152 may be surface coated with a sealing liquid, e.g. by immersion in the sealing liquid, to make the auxiliary housing 152 fluid-tight. Alternatively or additionally, terminals of the auxiliary component 150 may be provided by insert moulding.

The main device part 110 comprises a main coupling part 130. The auxiliary component 150 comprises an auxiliary coupling part 170. The auxiliary coupling part 170 and the main coupling part 150 are adapted to be coupled. The main coupling part 130 is adapted to couple with the auxiliary coupling part 170. The auxiliary coupling part 170 is adapted to couple with the main coupling part 130.

The main coupling part 130 comprises one or more main terminals 132. The one or more main terminals 132 may be electrically connected to a light emitter and an image sensor of the main device part 110.

The auxiliary coupling part 170 comprises one or more auxiliary terminals 172. The one or more auxiliary terminals 172 and the one or more main terminals 132 are adapted to connect, when the auxiliary coupling part 170 is coupled with the main coupling part 130. The one or more auxiliary terminals 172 are adapted to connect to the one or more main terminals 132. The one or more main terminals 132 are adapted to connect to the one or more auxiliary terminals 172.

The main coupling part 130 has a main surface 140 with a main primary engagement member 142. The main primary engagement member 142 may be a recess, as illustrated. Alternatively, the main primary engagement member 142 may be a protrusion. The main primary engagement member 142 may be another suitable engagement member.

The auxiliary coupling part 170 has an auxiliary primary engagement member 182 adapted to engage with the main primary engagement member 142, such as to restrict movement of the auxiliary primary engagement member 182 along the main surface 140. For example, the auxiliary primary engagement member 182 may be a cooperating member of the main primary engagement member 142. For example, the auxiliary primary engagement member 182 may be a protrusion, as illustrated. Alternatively, the auxiliary primary engagement member 182 may be a recess. The auxiliary primary engagement member 182 may be another suitable engagement member.

The main coupling part 130 comprise a primary surface 146. The primary surface 146 accommodates exposed portions of the one or more main terminals 132. The primary surface 146 may be substantially perpendicular to the main surface 140, as illustrated.

The main coupling part 130 may have a main secondary engagement member, and the auxiliary coupling part may have an auxiliary secondary engagement member adapted to engage with the main secondary engagement member, such as to restrict movement of the auxiliary secondary engagement member perpendicular to the main surface 140. The primary surface 146 may be between the main primary engagement member 142 and the main secondary engagement member.

Figure 4:
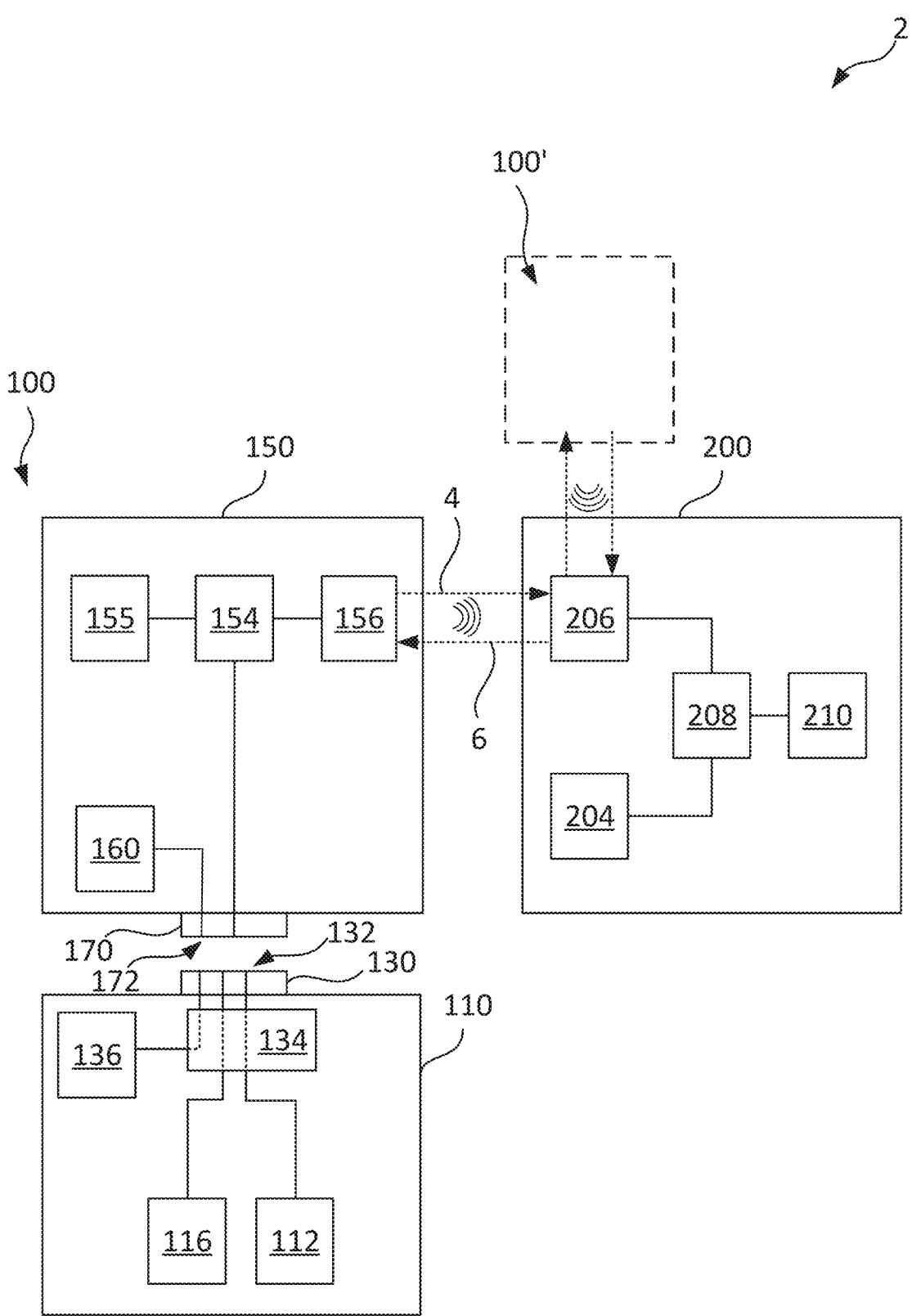
FIG. 4 is a block diagram schematically illustrating a medical visualisation system, FIG. 5 schematically illustrates an exemplary operating room.

FIG. 4 is a block diagram schematically illustrating a medical visualisation system 2, such as the medical visualisation system 2 as described with respect to previous figures.

The medical visualisation system 2 comprises an exemplary medical visualisation device 100, such as the medical visualisation device 100 as described with respect to previous figures, and an exemplary monitor device 200, such as the monitor device 200 as described with respect to previous figures.

The medical visualisation device 100, as the medical visualisation device 100 of FIGS. 2 and 3, comprises a main device part 110 and an auxiliary component 150 couplable to the main device part 110.

The main device part 110 comprises an image sensor 112 adapted to generate image data indicative of a view from the main device part 110, a light emitter 116 adapted to provide illumination of the view, and a main coupling part 130 having one or more main terminals 132 electrically connected to the light emitter 116 and the image sensor 112. The main device part 110 may further comprise a safety circuit 134 and a device identifier 136.

The device identifier 136 may comprise device identifier information, such as serial number of the main device part 110, which may uniquely identify the main device part 110. Also, the device identifier information may be indicative of the type of visualisation device, e.g. whether the medical visualisation device 100 and/or the main device part 110 is a bronchoscope or a laryngoscope. Alternatively or additionally, the device identifier information may be indicative of the brand of the visualisation device, production version, batch number etc.

The device identifier 136 may include an electronically readable memory, such as an EPROM, RFID, NFC or similar. In other examples the device identifier may be a QR-code, bar-code or similar. The device identifier 136 may be connected to the one or more main terminals 132, as illustrated. However, in other exemplary medical visualisation devices, the device identifier 136 may be readable without the necessity to establish an electrical contact. For example, the device identifier 136 may be readable by means of a short-range communication circuit, such as an RFID or NFC circuit. In other exemplary medical visualisation devices, the device identifier 136 may be optically read, e.g., wherein the device identifier is a QR-code or bar code.

The auxiliary component 150 comprises an auxiliary coupling part 170 adapted to couple with the main coupling part 130. The auxiliary coupling part 170 comprises one or more auxiliary terminals 172 adapted to connect to the one or more main terminals 132 of the main coupling part 130, when the auxiliary coupling part 170 is coupled with the main coupling part 130.

The auxiliary component 150 comprises a device processing unit 154 and a device wireless communication module 156. The auxiliary component 150 may further comprise an auxiliary memory 155, such as a flash memory or other suitable electronic memory. The device processing unit 154 may be adapted to read and/or write to/from the auxiliary memory 155. The auxiliary component 150 may further comprise a battery 160, as illustrated. The battery 160 may be a rechargeable battery.

The device processing unit 154 is electrically connected to the one or more auxiliary terminals 172 and adapted to receive the image data from the image sensor 112, when the auxiliary component 150 is coupled to the main device part

110. The device processing unit 154 may further be adapted to encode the image data to provide encoded image data based on the image data, and transmit the image data and/or the encoded image data to the device wireless communication module 156, for wireless transmission to the monitor device 200. For example, the device processing unit 154 may encode the image data in accordance with a wireless video transmission protocol.

The device wireless communication module 156 is connected to the device processing unit 154 and adapted to communicate with a monitor wireless communication module 206 of the monitor device 200. The device wireless communication module 156 is adapted to receive the image data and/or the encoded image data from the device processing unit 154 and transmit the image data and/or the encoded image data using a downstream data channel 4 to the monitor wireless communication module.

The device processing 154 unit may be adapted to obtain the device identifier information from the device identifier 136, e.g. via the one or more auxiliary terminals 172 and one or more main terminals 132.

The battery 160 is adapted to power the medical visualisation device 100. The battery 160 is adapted to power the electronic elements of the auxiliary component 150, such as the device processing unit 154 and/or the device wireless communication module. For example, the battery 160 may be connected to the electronic components of the auxiliary component 150, e.g. the device processing unit 154 and/or the device wireless communication module. The battery 160 is electrically connected to the one or more auxiliary terminals 172, such as to power the main device part 110 and/or the electronic elements thereof, when the auxiliary component 150 is coupled to the main device part 110, such as when the main coupling part 130 is coupled with the auxiliary coupling part 170. For example, the battery 160 may be adapted to power the image sensor 112 and light emitter 114 of the main device part 110. The battery 160 may be adapted to power the device identifier 136.

The safety circuit 134 may be adapted to prevent excessive current to the elements of the main device part 110, such as the light emitter 116, the image sensor 112 and/or the device identifier 136. For example, the one or more main terminals 132 may be electrically connected to the light emitter 116, the image sensor 112 and/or the device identifier 136 via the safety circuit. Thereby, the elements of the main device part 110 may be protected, in case an auxiliary component able to power another, more power consumptive, device part, is coupled to the main device part 110.

The monitor device 200 comprises the monitor wireless communication module 206 and a monitor processing unit 208. The monitor device 200 may comprise a monitor memory 210, such as a Flash memory or other suitable electronic memory.

The monitor device 200 may further comprise a display 204, as illustrated. In an alternative example, such as exemplified for the monitor device 200' in FIG. 1B, the monitor device may be couplable to an external display. In either case, the display 204 may be operable to display a live representation of the image data indicative of the view 114 from the visualisation device 100. The display 204 may be touch sensitive display.

The monitor wireless communication module 206 is adapted to communicate with the device wireless communication module 156. The monitor wireless communication module 206 is adapted to receive image data and/or encoded image data using the downstream data channel 4 from the device wireless communication module 156 to the monitor wireless communication module 206. The monitor wireless communication module 206 may further be adapted to transmit the received image data and/or encoded image data to the monitor processing unit 208.

The monitor processing unit 208 is adapted to receive the image data and/or the encoded image data from the monitor wireless communication module 206. The monitor processing unit 208 may further be adapted to decode the encoded image data. The monitor processing unit 208 may be adapted to cause the display 204 to display a live representation of the image data.

The monitor wireless communication module 206 may further be adapted to transmit settings data using an upstream data channel 6 from the monitor wireless communication module 206 to the device wireless communication module 156. The device wireless communication module 156 is adapted to receive settings data using the upstream data channel 6.

The monitor processing unit 208 may be adapted to generate and/or provide the settings data to the monitor wireless communication module 206 for transmission to the medical visualisation device.

For example, the monitor processing unit 208 may generate the settings data based on the image data, e.g. to adjust settings of one or more components of the medical visualisation device 100, e.g. the light emitter 116 and/or the image sensor 112. The device processing unit 154 may be adapted to receive the settings data from the device wireless communication module 156 and adjust settings of one or more components of the medical visualisation device 100 based on the settings data. For example, the settings data may be indicative of adjustment of the image sensor, e.g. including colour, contrast, gain, and/or exposure settings. Alternatively or additionally, the settings data may be indicative of adjustment of the light emitter, e.g. including current, brightness, and/or PWM settings. By utilizing the upstream data channel 6 to transmit settings data, the monitor processing unit 208 may process the image data received and continuously adjust settings of the light emitter 116 and/or image sensor 112, to enhance the image quality. Thereby, the heavier computational image analysis may be performed in the monitor device 200, allowing the medical visualisation device 100 to draw less power, needing less battery capacity and effectively allowing the medical visualisation device to be lighter and more compact.

The wireless communication between the medical visualisation device 100 and the monitor device 200 may be established by activation of a pairing sequence, e.g. by the user pressing a pairing button on the monitor device 200 and on the medical visualisation device 100. In response to activation of the pairing sequence, the device processing unit 154 and the monitor processing unit 208 cause the device wireless communication module 156 and the monitor wireless communication module 206 to exchange information to setup a data link for subsequent data transfer, e.g. including information regarding communication channel for the data link, identification details of the respective devices, etc.

After establishing the data link, an initialisation sequence may be performed. Alternatively, the initialisation sequence may be performed in response to the auxiliary component 150 and the main device part 110 being coupled. The initialisation sequence may include that the monitor processing unit 208 receives device identifier information from the device identifier 136. Based on the device identifier information, the monitor processing unit 208 is able to process the image data received from the medical visualisation device 100. Based on the device identifier information, the monitor processing unit 208 may generate and/or provide initial settings data to the monitor wireless communication module 206 for transmission to the medical visualisation device 100, such as to the device processing unit 154, which may adjust settings of one or more components of the medical visualisation device 100 based on the initial settings data. Thereby, the settings of the one or more components may be set to a default or initial value, which may be dependent on various information related to the specific device, i.e. based on the device identifier information. Similar to the settings data, explained above, the initial settings data may be indicative of adjustment of the image sensor, e.g. including colour, contrast, gain, and/or exposure settings. Alternatively or additionally, the initial settings data, like the settings data, may be indicative of adjustment of the light emitter, e.g. including current, brightness, and/or PWM settings.

The initialisation sequence may further include that a designated user interface is loaded on the monitor device 200. For example, a designated user interface may be loaded based on the device identifier information, e.g. depending on whether the medical visualisation device 100 and/or the main device part 110 is a bronchoscope, a laryngoscope, or another visualisation device.

Further, FIG. 4 also illustrates that the medical visualisation system 2 may comprise a plurality of medical visualisation devices, e.g. the first medical visualisation device 100 as already described and a second medical visualisation device 100'. The second medical visualisation device 100' may generally comprise the similar features and components as the first medical visualisation device 100 and is therefore, for brevity, not described in further details. As seen the monitor device 200, such as the monitor wireless communication module 206 may be adapted to communicate with the second medical visualisation device 100', such as with a device wireless communication module of the second medical visualisation device 100'. For example, the monitor wireless communication module 206 may be adapted to receive image data and/or encoded image data using a downstream data channel from the second medical visualisation device 100'. The monitor processing unit 208 may be adapted to cause the display 204 to display a live representation of the image data of the second medical visualisation device 100', e.g. simultaneously with display of the image data of the first medical visualisation device 100, e.g. side by side or picture-in-picture, or in another arrangement.

The monitor wireless communication module 206 may further be adapted to transmit settings data using an upstream data channel from the monitor wireless communication module 206 to the second medical visualisation device 100', such as to a device wireless communication module of the second medical visualisation device, as similarly described with respect to the medical visualisation device 100.

Figure 5:
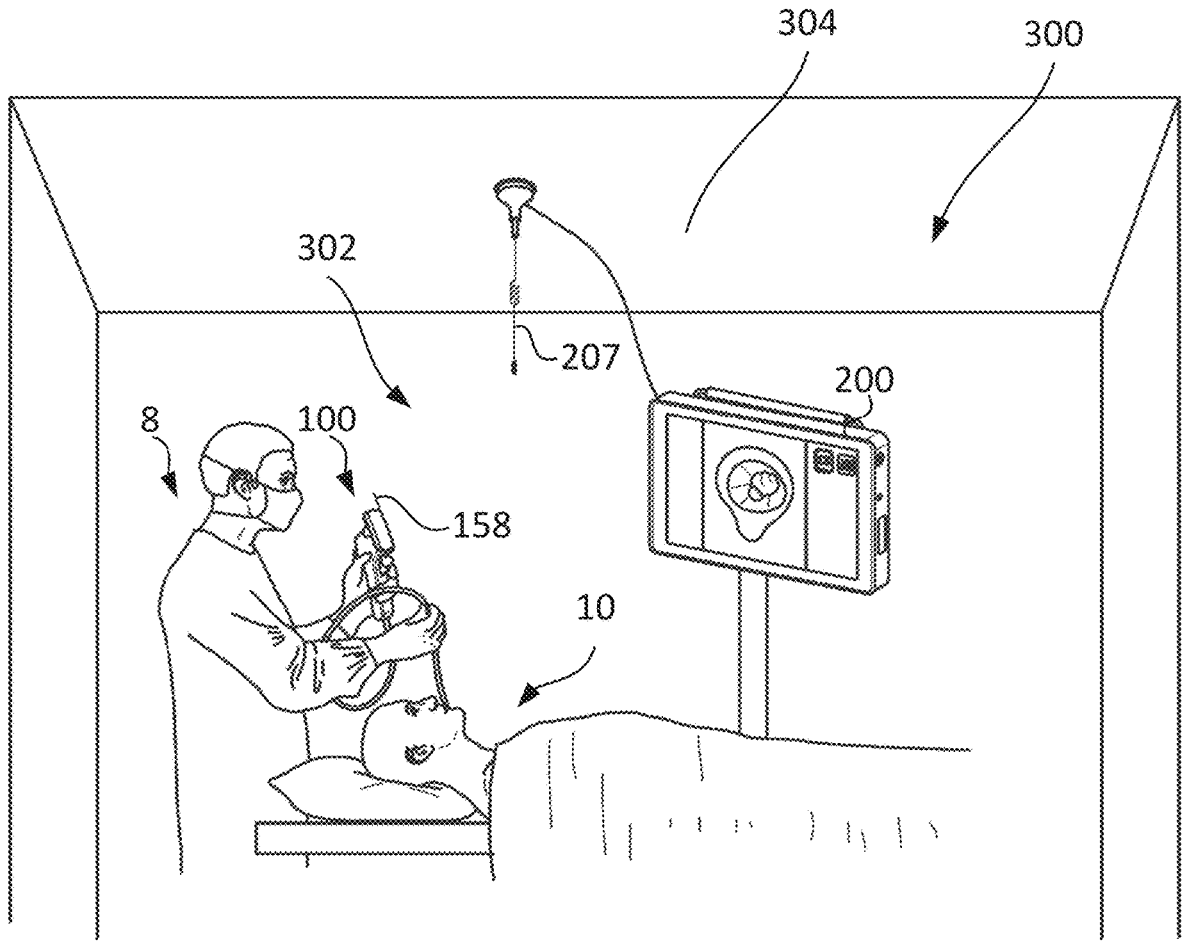

FIG. 5 schematically illustrates an exemplary operating room 300 with an operating setting 302, wherein an endoscope procedure is being performed on a patient 10 by an operator 8 of a medical visualisation device 100. The operator 8 is seeing the view from the medical visualisation device 100 at the monitor device 200.

The monitor wireless communication module of the monitor device 200 comprises a monitor antenna 207, and the device wireless communication module of the medical visualisation device 100 comprises a device antenna 158. Here the device antenna 158 is shown for the purpose of illustration, alternatively, the device antenna 158 may be positioned inside a housing of the medical visualisation device 100.

The image data from the medical visualisation device 100 is transmitted to the monitor device by wireless communication via the device antenna 158 and the monitor antenna 207. To ensure constant wireless transfer of the image data, it may be advantageous to ensure or promote line of sight between the device antenna 158 and the monitor antenna 207. Therefore, the monitor antenna 207 is positioned external to a housing of the monitor 200. The monitor antenna 207 may be positioned at a distance from the housing, e.g. of more than 2 meters. The monitor antenna 207 may be adapted to be positioned above the operating setting 302, such as at the ceiling 304 of the operating room 300, as illustrated.

Figure 6:
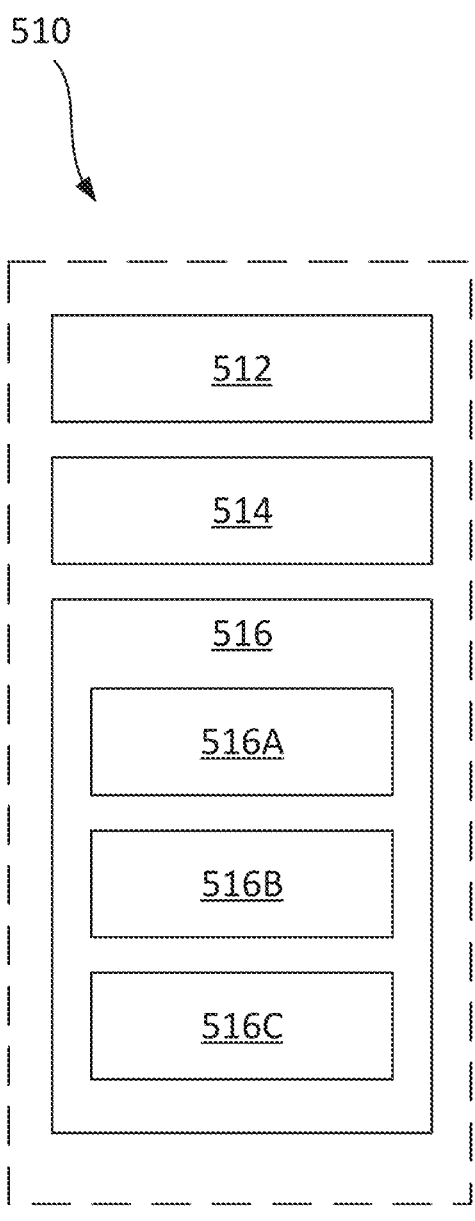
FIG. 6 is a block diagram schematically illustrating exemplary initial data, FIG. 7 schematically illustrates an exemplary medical visualisation device, FIG. 8 schematically illustrates an exemplary monitor device, FIG. 9 schematically illustrates an exemplary monitor device.

FIG. 6 is a block diagram schematically illustrating exemplary initial data 510 of the auxiliary memory. The auxiliary memory 155 of the auxiliary component 150 (cf. FIG. 3) may store initial data 510 for being loaded by the monitor device. For example, the initial data 510 may be loaded by the monitor device upon initialisation of a new procedure, e.g. upon establishing connection between the auxiliary component and the monitor device. The auxiliary component may be configured to transmit and/or be enablable to transmit the initial data to the monitor device, e.g. using an auxiliary communication interface. The monitor processing unit may be adapted to receive the initial data 510 and adjust one or more parameters of the medical visualisation system based on the initial data 510.

For example, the initial data 510 may comprise patient data 512, e.g. of the patient on which the procedure is about to be performed. Thus, the monitor device may retrieve and store patient data from the auxiliary component. For example, the auxiliary component may be adapted to follow the patient, and upon performing a procedure, by using the "personal" auxiliary component of the patient, the correct data of the patient is automatically received by the monitor device, and the monitor device may be adapted to associate the patient data with the image data, such as any stored still images or video sequences. The patient data 512 may include patient name, social security number, etc. The patient data 512 may also include information about the procedure to be performed, medical history, information about allergies, etc. Thereby, all relevant information may be right at hand for the operator of the medical visualisation system.

Alternatively or additionally, the initial data 510 may comprise operator data 514 indicative of the operator performing the medical visualisation procedure. Thus, the monitor device may retrieve and store operator data from the auxiliary component, such as to log information about the operator performing the procedure. For example, the auxiliary component may be adapted to follow the operator, and upon performing a procedure, by using the "personal" auxiliary component of the operator, the data of the operator is automatically received by the monitor device, and the monitor device may be adapted to associate the operator data with the image data, such as any stored still images or video sequences. The operator data 514 may alternatively or additionally be indicative of a username or other logon credentials of the operator, such as to facilitate and easier logon process, e.g. of the monitor device and/or an associated IT-system.

The auxiliary memory may also work as a storage device for storing image data files and/or video sequence files. Thus, the monitor processing unit and/or the device processing unit may store an image data file and/or video sequence file in the auxiliary memory in response to receipt of a user input signal indicative of a user activating an image capture button, as described above in relation to FIG. 1A. In accordance with the above, the monitor processing unit and/or the device processing unit may be adapted to associate the patient data and/or the operator data with the image data file. Thereby, the files stored during the procedure may be conveniently stored on the auxiliary component and follow either the patient or the operator for later retrieval.

Alternatively or additionally. The initial data 510 may comprises operator setup data 516 associated with the operator performing the medical visualisation procedure. Thus, this may be particularly useful when the initial data 510 also comprises operator data 514.

The operator setup data 516 may include image parameters 516A, e.g. including settings for hue, saturation, brightness, contrast, and/or sharpness. The monitor processing unit may, in response to receiving the initial data 510, adjusts image parameters of the live representation of the image data displayed on the display in accordance with the image parameters 516A of the operator setup data 516. Thus, the system may conveniently adjust parameters to be in accordance with preferences of the operator, thereby reducing unnecessary time to setup the monitor device in accordance with individual preferences of an operator.

The medical visualisation system, such as the monitor device and/or the medical visualisation device may, as previously described, comprise one or more buttons adapted to receive user inputs. The operator setup data 516 may include button settings 516B indicative of functions assigned to one or more of the buttons, e.g. on the handle of the main device part or on the monitor device. The monitor processing unit may, in response to receiving the initial data 510, assign functions to the one or more of the buttons in accordance with the button settings 516B of the operator setup data 516. Thus, the system may conveniently setup the devices in accordance with preferences of the operator, thereby reducing unnecessary manual setup time prior to a procedure.

The monitor processing unit and/or the device processing unit may be adapted to perform tasks based on spoken inputs. For example, the monitor device may comprise a microphone, or a microphone may be coupled to the monitor device, adapted to register utterances from the operator Thus, the operator setup data 516 may include voice control data 516C associated with the operator, e.g. including keywords, training data etc. The monitor processing unit, after receiving the initial data 510, may identify tasks to be performed based on the spoken inputs and the voice control data 516C of the initial data 516.

The monitor processing unit may be adapted to store new operator setup data 516, and/or to update the currently stored operator setup data 516 in the auxiliary memory based on a current set of settings of the monitor device. For example, the monitor processing unit may store or update operator setup data in the auxiliary memory in response to receipt of a user input signal indicative of a user requesting storing of the current set of settings. For example, a designated button may be provided, or a certain input, e.g. pressing a predetermined button for more than a predetermined time, may activate a storing/updating procedure of the operator setup data 516.

Figure 7:
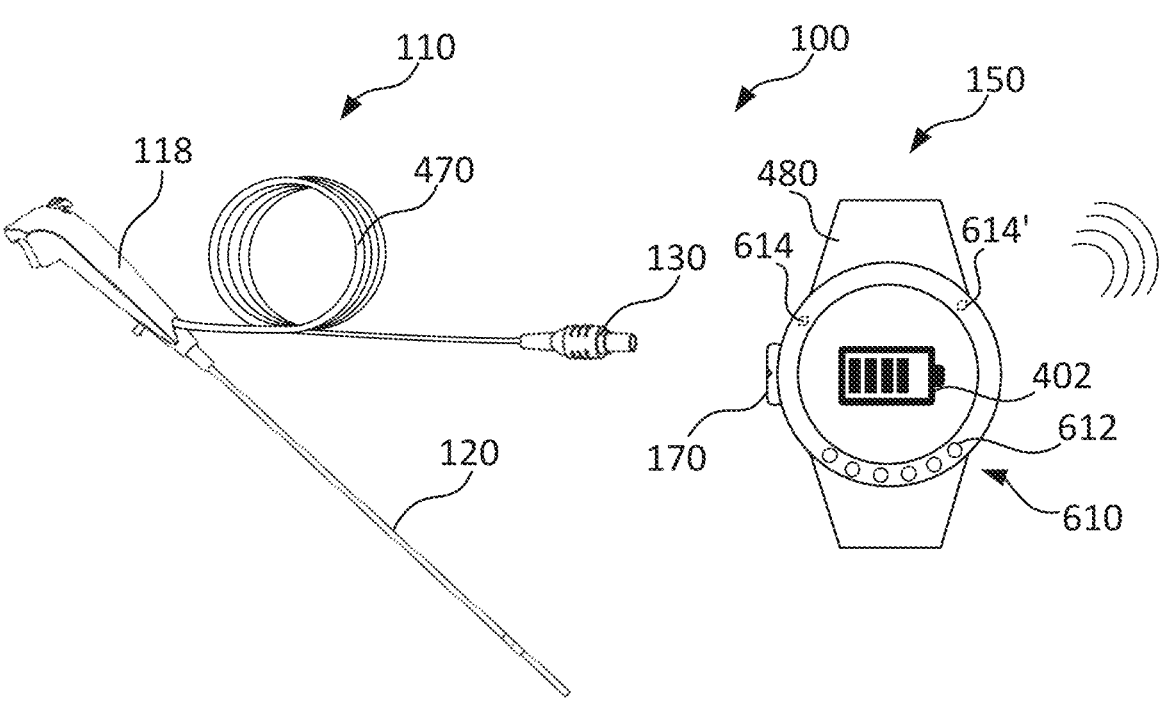

FIG. 7 schematically illustrates an exemplary medical visualisation device 100, wherein the auxiliary component 150 is a wearable device, such as a wristwatch. The auxiliary component 150 comprises a wearing element 480, such as a strap, as illustrated. The auxiliary component 150 being a wearable device may be particularly advantageous if the auxiliary component 150 is to follow a certain person, e.g. if the auxiliary memory comprises personal data, such as patient data, operator data, or operator settings data.

In the illustrated example, the medical visualisation device 100 comprises a main device part 110 with one or more flexible device wires 470. The flexible device wire(s) 470 extends between the main coupling part 130 and the handle 118 of the main device part 110. The main terminals of the main coupling part 130 may be electrically connected to the light emitter and the image sensor (e.g. located at the distal end of the insertion tube 120) through the flexible device wire(s) 470. The flexible device wire(s) 470 may be flexible to enable a user to bend the wires, such as to position the main coupling part 130 appropriately to attach to the auxiliary coupling part 170 of the auxiliary component 150.

The auxiliary component 150, as illustrated, comprises a battery indicator 402. The battery indicator 402 is indicative of remaining capacity of the battery. The battery indicator 402 may be a graphical representation and/or one or more LEDs or other suitable means for providing an indication of remaining battery capacity. The battery indicator 402 may be provided using an e-ink display, e.g. such that the battery indicator 402 only uses power when updating the display, e.g. once every day when not being used.

As indicated, the battery indicator 402 may comprise a plurality of bars (e.g. five) indicative of capacity of the battery, e.g. fewer bars displayed for less battery capacity. The battery indicator 402 comprising a plurality of bars, may be combined with being lit in different colours, e.g. green (indicative of full or near full charge), yellow (medium capacity), red (low capacity). The battery indicator 402 may be flashing, e.g. red, when the battery capacity is below a threshold capacity.

The auxiliary component may comprise a button adapted to receive a user input, and the auxiliary device may be adapted such that, in response to receiving the user input on button, the battery indicator 402 becomes visible and indicates the present battery capacity. For example, the battery indicator 402 may, in response to receiving the user input, light up the battery indicator 402 in accordance with the current battery capacity. The battery indicator 402 may, in response to receiving the user input, display the plurality of bars in accordance with the current battery capacity. Thus, battery power may be conserved by displaying the indication of battery capacity "on demand" when a user presses a button. Alternatively or additionally, when the battery capacity is critically low, the battery indicator 402 may indicate battery capacity, e.g. by flashing red, e.g. regardless of receiving or not receiving user input.

The auxiliary component 150 comprises a secondary auxiliary coupling part 610 having one or more secondary auxiliary terminals 612, e.g. electrically connected to the device processing unit and/or the one or more auxiliary terminals of the auxiliary coupling part 170. The secondary auxiliary coupling part 610 may provide for a wired coupling with the monitor device in case the wireless connection fails.

The secondary auxiliary coupling part 610 comprise secondary auxiliary magnetic elements 614, 614'. The secondary auxiliary magnetic elements 614, 614' may be adapted to align the secondary auxiliary terminals 612 with monitor terminals and couple the secondary auxiliary coupling part 610 with the monitor coupling part. The secondary auxiliary magnetic elements comprise a first secondary auxiliary magnetic element 614 and a second secondary auxiliary magnetic element 614'. The first secondary auxiliary magnetic element 614 and the second secondary auxiliary magnetic element 614' may have opposite polarity, e.g. the first secondary auxiliary magnetic element 614 may be north, and the second secondary auxiliary magnetic element 614' may be south.

Figure 8:
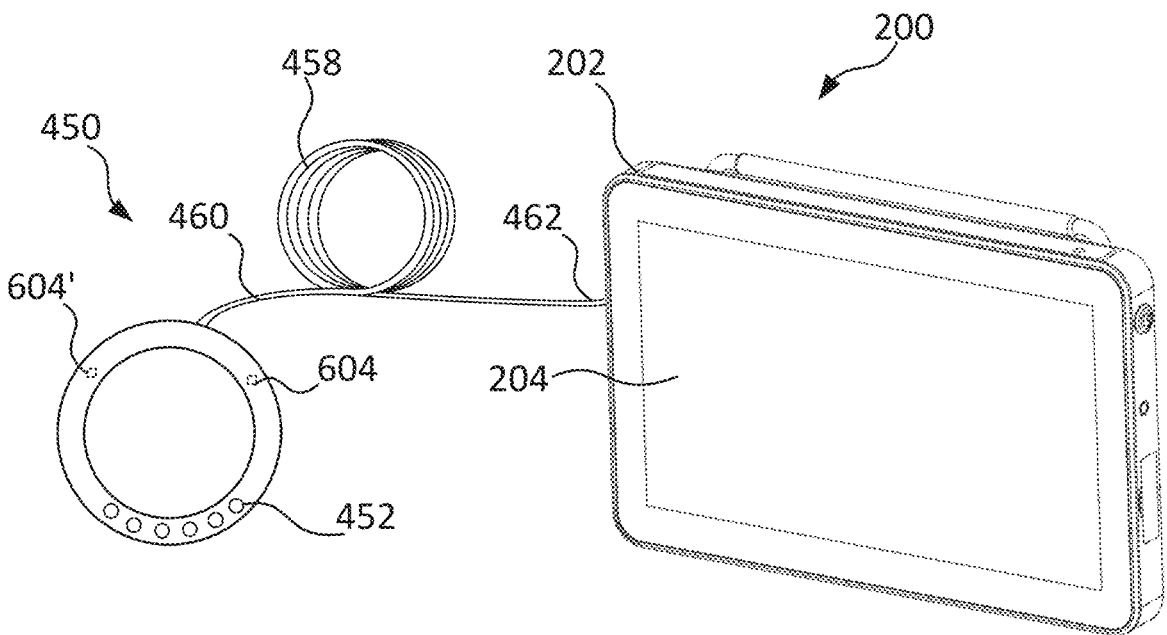

FIG. 8 schematically illustrates an exemplary monitor device 200, as previously described. The monitor device 200, as illustrated in FIG. 8, further comprises a monitor coupling part 450. The monitor coupling part 450, in the illustrated example, is adapted to couple with the secondary auxiliary coupling part 610 of the auxiliary component 150, as illustrated in FIG. 7. Thus, a wired backup solution is provided in case wireless transmission between the medical visualisation device 100 and the monitor device 200 is not possible, e.g. if the battery of the visualisation device 100 is empty. By providing a wired backup coupling between the monitor device and the auxiliary component 150, the initial data being provided in the auxiliary memory of the auxiliary component 150 may still be read by the monitor device, even using the backup solution.

The monitor coupling part 450 comprises one or more monitor terminals 452. The monitor terminal(s) 452 is adapted to connect to the secondary auxiliary terminal(s) 612 of the secondary auxiliary coupling part 610, when the monitor coupling part 450 is coupled with the secondary auxiliary coupling part 610. The monitor processing unit may be electrically connected to the more monitor terminal (s) 452. Furthermore, the monitor processing unit may be adapted to receive the image data, via the monitor coupling part 450, from the image sensor of the medical visualisation device 100 and cause the display 204 to display a live representation of the image data.

The monitor device 200, such as the monitor coupling part 450, may comprise one or more flexible monitor wires 458. The monitor terminal(s) 452 is arranged at a distal end 460 of the one or more flexible monitor wires 458. A housing of the monitor device 200, such as the first housing 202, is arranged at the proximal end 462 of the flexible monitor wire(s) 458. A coupling plug (not shown) may be coupled to the proximal end of the flexible monitor wire(s) 458 for coupling the flexible monitor wire(s) 458 to the housing of the monitor device 200. The monitor terminal(s) 452 is electrically connected to the monitor processing unit through the one or more flexible monitor wires 458. The flexible monitor wire(s) 458 may be flexible to enable a user to bend the wires, such as to arrange the monitor coupling part appropriately to attach to the main coupling part.

The monitor coupling part 450 is adapted to couple with the secondary auxiliary coupling part 610 (see FIG. 7). The one or more monitor terminals 452 is adapted to connect to the one or more secondary auxiliary terminals 612 of the secondary auxiliary coupling part 610. The monitor processing unit may be adapted to, e.g. when the monitor coupling part 450 is coupled with the secondary auxiliary coupling part 610, receive the image data and/or the encoded image data from the auxiliary component 150.

The monitor coupling part 450 comprises monitor magnetic elements 604, 604'. The secondary auxiliary magnetic elements 614, 614' (see FIG. 7) and the monitor magnetic elements 604, 604' are adapted to align the secondary auxiliary terminals 612 and the monitor terminals 452 and couple the secondary auxiliary coupling part 610 and the monitor coupling part 450. Thus, the user may easily attach the monitor coupling part 450 and the secondary auxiliary coupling part 610 by positioning the part of the monitor coupling part 450 comprising the monitor terminals 452 and the monitor magnetic elements 604, 604' onto the secondary auxiliary coupling part 610.

Figure 9:
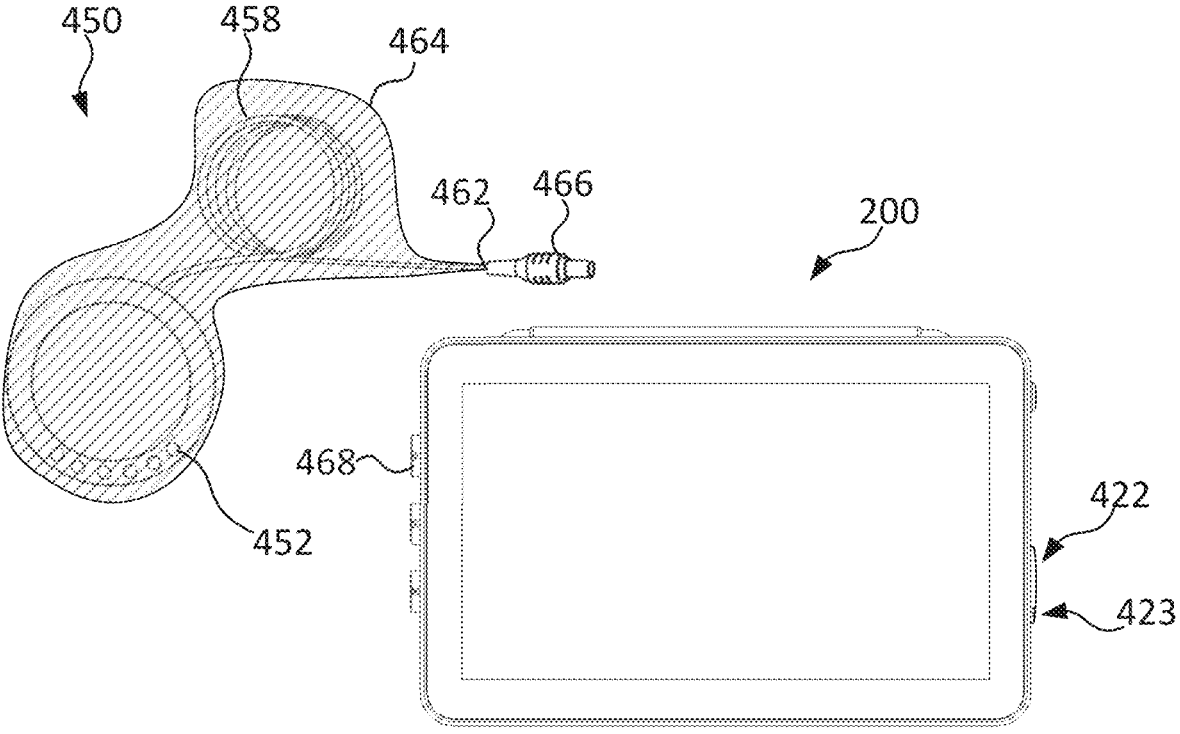

FIG. 9 schematically illustrates an exemplary monitor device 200, as described in relation to FIG. 8.

As illustrated in FIG. 9, the flexible monitor wire(s) 458 and the monitor terminal(s) 452 may be enclosed in a sealed package 464, and a coupling plug 466 may be coupled to the proximal end 462 of the flexible monitor wire(s) 458. The coupling plug 466 may be arranged outside the sealed package 464, such as to allow connecting the coupling plug 466 with the coupling socket 468 of the monitor device 200 configured to receive the coupling plug 466. The monitor coupling part 450 may thereby be connected before being needed and stay sterile, and when being needed the operator only needs to open the sealed package 464 and couple the monitor coupling part 450 with the secondary auxiliary coupling part of the auxiliary component. The monitor coupling part 450, e.g. the coupling plug 466, may indicate, e.g. by light or sound, if the sealed devices are not properly working prompting replacement, e.g. based on a self-test of the electronic components.

Alternatively, the monitor device 200, such as the processing unit of the monitor device, may be able to do an electronic test of the electronic components of the sealed device and notify a user, if the sealed devices are not properly working.

The monitor device 200 may further comprise, e.g. in addition to the monitor coupling part 450, a component socket 422 adapted to engage with the auxiliary component 150. For example, the component socket 422 may be adapted to transfer the initial data from the auxiliary component 150 to the monitor device 200. The component socket 422 may also or alternatively be adapted to store and/or charge the auxiliary component 150, and/or be adapted to pair the wireless communication modules of the monitor device 200 and the auxiliary component 150. The component socket 422 may comprise one or more monitor terminals 423, which may comprise charging terminals and/or pairing terminals. The auxiliary component 150 may be held in place in the component socket 422 by magnetic elements.

Figure 10:
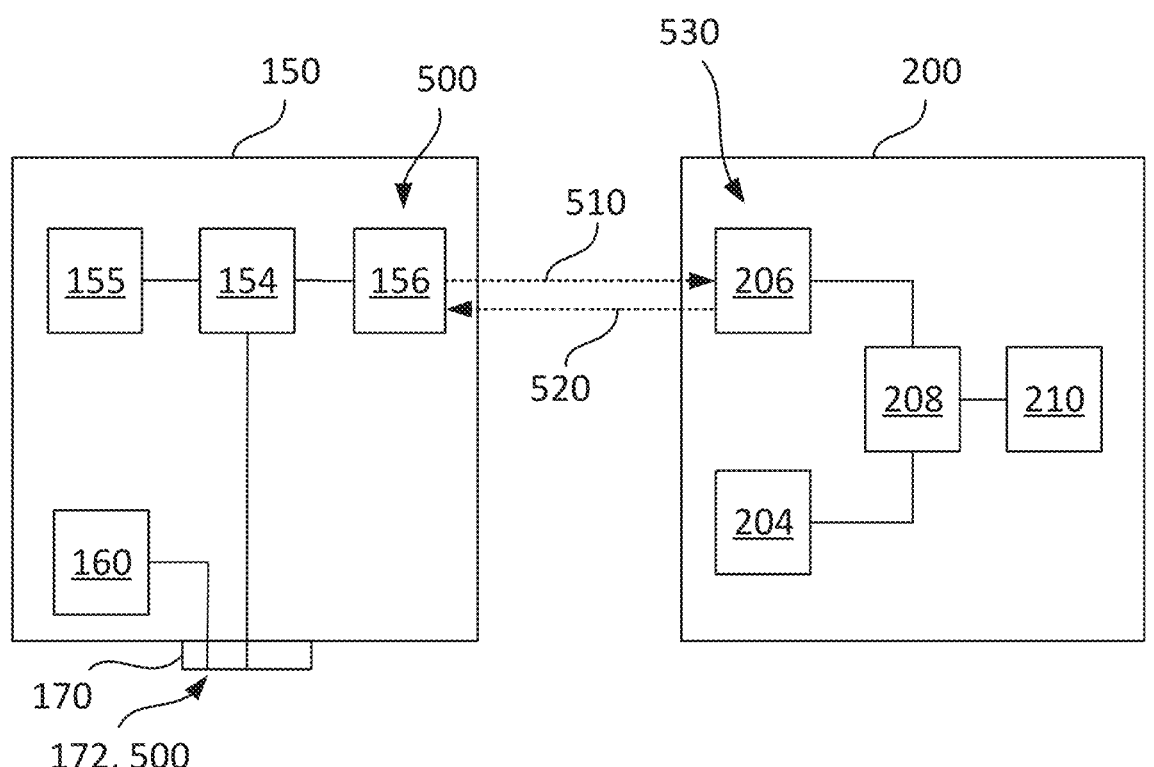
FIG. 10 is a block diagram schematically illustrating an auxiliary component and a monitor device.

FIG. 10 is a block diagram schematically illustrating an auxiliary component 150 and a monitor device 200, such as the auxiliary component and the monitor device previously described, e.g. such as the auxiliary component and the monitor device of FIG. 4. The auxiliary component 150 comprises a plurality of auxiliary communication interfaces 500 including the device wireless communication module 156 and the auxiliary terminals 172 of the auxiliary coupling part 170, as described with respect to FIG. 3. The monitor device comprises at least one monitor communication interface 530, including the monitor wireless communication module 206, as described with respect to FIG. 3. The initial data 510, as described in relation to FIG. 6, may be transmitted from the auxiliary memory 155 to the monitor device 200 using the device wireless communication module 156 and the monitor wireless communication module 206. The monitor processing unit 208 may receive the initial data 510 and adjust the medical visualisation system based on the initial data 510, as explained in relation to FIG. 6.

The device processing unit 154 may be adapted to encode the initial data 510 together with the image data in the encoded image data transmitted from the device wireless communication module 156 to the monitor wireless communication module, as explained in relation to FIG. 4. Thus, the initial data 510 may be transmitted to the monitor device 200 embedded in the encoded image data.

Alternatively or additionally, the device wireless communication module 156 may transmit the initial data 510 to the monitor wireless communication module 206 during an initialisation procedure before transmitting the image data/encoded image data.

The monitor processing unit may store an image data file 520 in the auxiliary memory 155, i.e. the monitor device may transfer the image data file 520 to the auxiliary component for being stored in the auxiliary memory 155 for later retrieval. The monitor processing unit may associate patient data and/or operator data, retrieved from the initial data 510, with the image data file 520.

Figure 11:
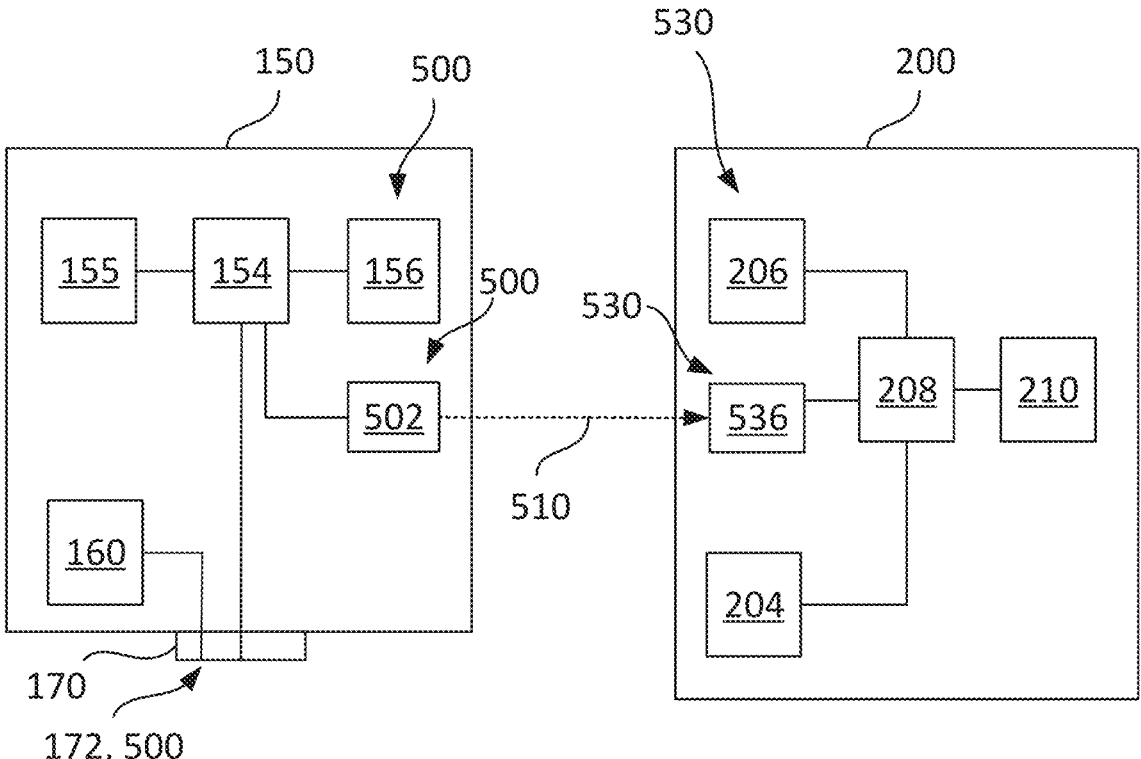
FIG. 11 is a block diagram schematically illustrating an auxiliary component and a monitor device.

FIG. 11 is a block diagram schematically illustrating an auxiliary component 150 and a monitor device 200, such as the auxiliary component and the monitor device previously described, e.g. such as the auxiliary component and the monitor device of FIG. 4. The auxiliary component 150 comprises a plurality of auxiliary communication interfaces 500 including the device wireless communication module 156 and the auxiliary terminals 172 of the auxiliary coupling part 170, as described with respect to FIG. 3. The monitor device comprises monitor communication interfaces 530, including the monitor wireless communication module 206, as described with respect to FIG. 3. Additionally, in the illustrated example, the auxiliary communication interfaces 500 and the monitor communication interfaces 530 each includes a short-range communication circuit 502, 536. The short-range communication circuits may be contactless, e.g. inductive, communication circuits, e.g. using near field communication (NFC) or similar technology. The initial data 510, as described in relation to FIG. 6, may be transmitted from the auxiliary memory 155 to the monitor device 200 using the short-range communication circuits 502, 536. For example, the initial data 510 may be transferred from the auxiliary component 150 to the monitor device 200 upon holding the auxiliary component near to a designated area of the monitor device 200 (e.g. the component socket 422 as illustrated in FIG. 9) for a predetermined period of time, the initial data 510 may be transmitted to the monitor device 200 and the monitor processing unit 208 may adjust the medical visualisation system based on the initial data 510, as explained in relation to FIG. 6.

Figure 12:
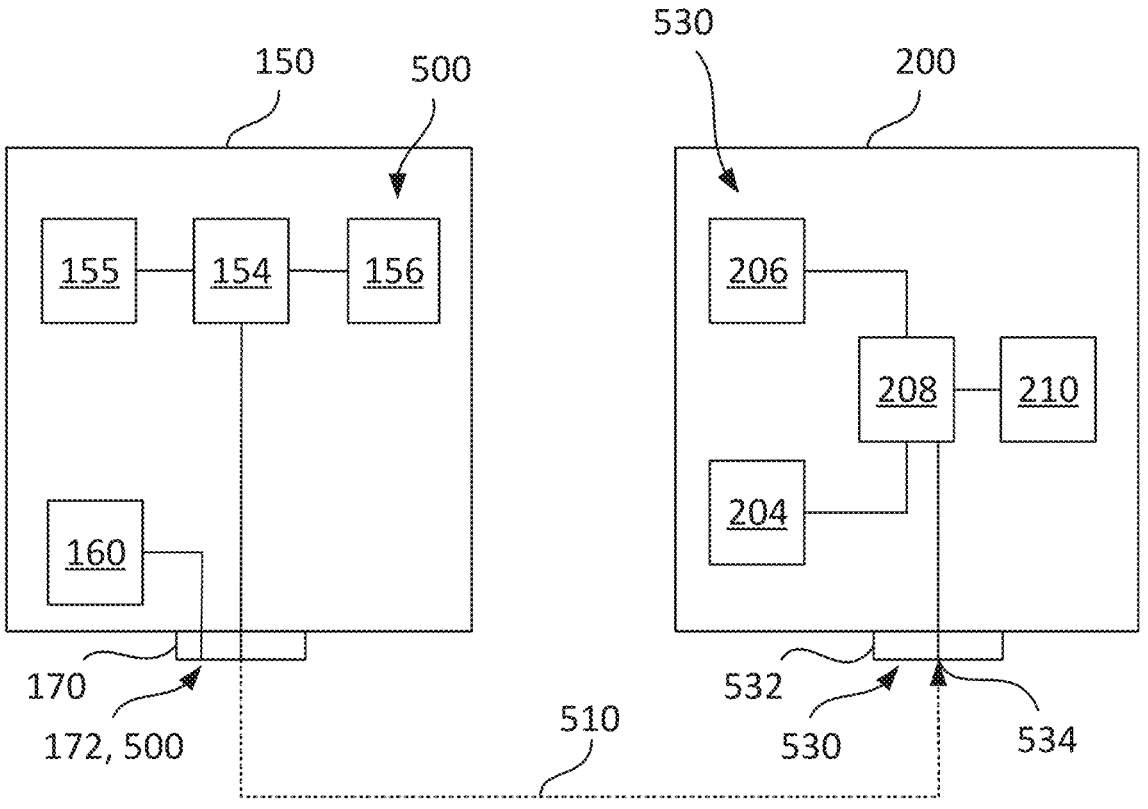
FIG. 12 is a block diagram schematically illustrating an auxiliary component and a monitor device.

FIG. 12 is a block diagram schematically illustrating an auxiliary component 150 and a monitor device 200, such as the auxiliary component and the monitor device previously described, e.g. such as the auxiliary component and the monitor device of FIG. 4. The auxiliary component 150 comprises a plurality of auxiliary communication interfaces 500 including the device wireless communication module 156 and the auxiliary terminals 172 of the auxiliary coupling part 170, as described with respect to FIG. 3. The monitor device comprises monitor communication interfaces 530, including the monitor wireless communication module 206, as described with respect to FIG. 3. Additionally, the monitor communication interfaces 530 includes a monitor coupling part 532 with exposed electrical terminals 534 to contact corresponding exposed electrical terminals of the auxiliary communication interface, such as the auxiliary terminals 172 of the auxiliary coupling part 170. The initial data 510, as described in relation to FIG. 6, may be transmitted from the auxiliary memory 155 to the monitor device 200 using the terminals 172, 534. For example, the initial data 510 may be transferred from the auxiliary component 150 to the monitor device 200 after the terminals 172, 534 being connected for a predetermined period of time and the monitor processing unit 208 may adjust the medical visualisation system based on the initial data 510, as explained in relation to FIG. 6.

The monitor coupling part 532 may be connectable with the auxiliary coupling part 170 as illustrated, i.e. using the same coupling part of the auxiliary component 150 also used for coupling the main device part and the auxiliary component 150. Alternatively or additionally, the monitor coupling part 532 may be connectable to a secondary auxiliary coupling part 610, as explained in relation to FIGS. 7 and 8. Thus, the monitor coupling part 450 of FIG. 8 may correspond to the monitor coupling part 532 of FIG. 12.

The disclosure has been described with reference to a preferred embodiment. However, the scope of the invention is not limited to the illustrated embodiment, and alterations and modifications can be carried out without deviating from the scope of the invention.

Throughout the description, the use of the terms "first", "second", "third", "fourth", "primary", "secondary", "tertiary" etc. does not imply any particular order or importance but are included to identify individual elements. Furthermore, the labelling of a first element does not imply the presence of a second element and vice versa.

LIST OF REFERENCES 2 medical visualisation system
4 downstream data channel
6 upstream data channel
8 operator
10 patient
100, 100' medical visualisation device
110 main device part
112 image sensor
114 view
116 light emitter
118 handle
119 device button, e.g. image capture button
120 insertion tube
122 distal tube portion
124 control button
125A first input direction
125B second input direction
126 bendable section
128A first bending direction
128B second bending direction
130 main coupling part
132 main terminal
134 safety circuit
136 device identifier
140 main surface
142 main primary engagement member
146 primary surface
150 auxiliary component
152 auxiliary housing
154 device processing unit
155 auxiliary memory
156 device wireless communication module
158 device antenna
160 battery
170 auxiliary coupling part
172 auxiliary terminal
182 auxiliary primary engagement member
200 monitor device
202 first housing
204 display
206 monitor wireless communication module 207 monitor antenna
208 monitor processing unit
210 monitor memory
212 monitor button, e.g. image capture button
300 operating room
302 operating setting
304 ceiling
402, 402' battery indicator
422 component socket
423 monitor terminal
450 monitor coupling part
452 monitor terminal
458 flexible monitor wire
460 distal end of flexible monitor wire
462 proximal end of flexible monitor wire
464 sealed package
466 coupling plug
468 coupling socket
470 flexible device wire
480 wearing element
500 auxiliary communication interface
502 short-range communication circuit
510 initial data
512 patient data
514 operator data
516 operator setup data
516A parameters
516B button setting
516C voice control data
520 image data file
530 monitor communication interface
532 monitor coupling part
534 electrical terminal
536 short range communication circuit
604, 604' monitor magnetic element
610 secondary auxiliary coupling part
612 secondary auxiliary terminals
614, 614' secondary auxiliary magnetic element

The invention claimed is:

1. A medical visualisation system comprising:
a monitor device including a first housing, one or more monitor communication interfaces including a monitor wireless transceiver, a monitor processor, and a monitor memory; and
a first medical visualisation device for performing a medical visualisation procedure, the first medical visualisation device including a main device component and an auxiliary component, the main device component comprising:
an image sensor configured to generate image data indicative of a view from the main device component,
a light emitter configured to provide illumination of the view, and
a main coupling component having one or more main terminals electrically connected to the light emitter and the image sensor, and
the auxiliary component comprising:
an auxiliary coupling component configured to removably couple with the main coupling component, the auxiliary coupling component comprising one or more auxiliary terminals configured to connect to the one or more main terminals of the main coupling component, when the auxiliary coupling component is coupled with the main coupling component,
a device processor electrically connected to the one or more auxiliary terminals and configured to receive the image data from the image sensor, when the auxiliary component is coupled to the main device component, and encode the image data to provide encoded image data based on the image data, one or more auxiliary communication interfaces including a device wireless transceiver connected to the device processor and configured to communicate with the monitor wireless transceiver of the monitor device, the device wireless transceiver being configured to receive the encoded image data from the device processor and transmit the encoded image data using a downstream data channel to the monitor wireless transceiver of the monitor device, and an auxiliary memory storing initial data, wherein the auxiliary component is configured to transmit the initial data to the monitor device, wherein the monitor processor is configured to receive the initial data and adjust one or more parameters of the medical visualisation system based on the initial data, wherein the monitor device is configured to cause a display to display a live representation of the image data, wherein the monitor processor or the device processor is configured to store an image data file in the auxiliary memory in response to receipt of a user input signal indicative of a user activating an image capture button, and wherein the image data file corresponds to the image data received when the image capture button was activated.

2. The medical visualisation system of claim 1, wherein the monitor device comprises the display, accommodated in the first housing.

3. The medical visualisation system of claim 1, wherein the initial data comprises patient data, and wherein the monitor processor is configured to associate the patient data with the image data.

4. The medical visualisation system of claim 1, wherein the initial data comprises operator data indicative of an operator performing the medical visualisation procedure, and wherein the monitor processor is configured to associate the operator data with the image data.

5. The medical visualisation system of claim 1, wherein the initial data comprises patient data and/or operator data indicative of an operator performing the medical visualisation procedure, and wherein the monitor processor is configured to associate the patient data and/or the operator data with the image data file.

6. The medical visualisation system of claim 1, wherein the initial data comprises operator setup data associated with the operator performing the medical visualisation procedure.

7. The medical visualisation system of claim 1, wherein the monitor processor is configured to store new operator setup data in the auxiliary memory based on a current set of settings of the monitor device.

8. The medical visualisation system of claim 7, wherein the monitor processor is configured to store the new operator setup data in the auxiliary memory in response to receipt of a user input signal indicative of a user requesting storing of the current set of settings, wherein optionally the user requesting storing of the current set of settings includes pressing a predetermined button for more than a predetermined time.

9. The medical visualisation system of claim 1, wherein the one or more monitor communication interfaces comprises exposed electrical terminals to contact corresponding exposed electrical terminals of the one or more auxiliary communication interfaces, and wherein the monitor processor is configured to receive the initial data via the exposed electrical terminals of the one or more monitor communication interfaces.

10. The medical visualisation system of claim 1, wherein the one or more monitor communication interfaces comprises a short-range communication circuit configured to inductively communicate with a corresponding short range communication circuit of the one or more auxiliary communication interface, and wherein the monitor processor is configured to receive the initial data via the short range communication circuit of the one or more monitor communication interfaces.

11. The medical visualisation system of claim 1, wherein the device processor is configured to encode the initial data together with the image data in the encoded image data, and wherein the initial data is transmitted to the monitor device embedded in the encoded image data.

12. The medical visualisation system of claim 1, wherein the device wireless transceiver transmits the initial data to the monitor wireless transceiver of the monitor device during an initialization procedure before encoding the image data and transmitting the encoded image data.

13. The medical visualisation system of claim 1, wherein the auxiliary component comprises a battery electrically connected to the one or more auxiliary terminals, the device processor and the device wireless transceiver, the battery being configured to power the device processor and the device wireless transceiver, the battery further being configured to power the image sensor and light emitter of the main device component when the auxiliary component is coupled to the main device component.

14. The medical visualisation system of claim 1, further comprising a second medical visualisation device including a second main device component including:

an image sensor configured to generate image data indicative of a view from the second main device component, a light emitter configured to provide illumination of the view, and a main coupling component having one or more main terminals electrically connected to the light emitter and the image sensor, the second main coupling component being configured to couple with the auxiliary coupling component of the auxiliary component.

15. The medical visualisation system of claim 14, wherein the first medical visualisation device is configured for a first clinical purpose and the second medical visualisation device is configured for a second clinical purpose, and wherein the first medical visualisation device is different from the second medical visualisation device.

16. The medical visualisation system of claim 14, wherein the image sensor of the first medical visualisation device is a first image sensor type and the image sensor of the second medical visualisation device is a second image sensor type different than the first image sensor type.

17. A medical visualisation system comprising:

a monitor device including a first housing, one or more monitor communication interfaces including a monitor wireless transceiver, a monitor processor, and a monitor memory; and a first medical visualisation device for performing a medical visualisation procedure, the first medical visualisation device including a main device component and an auxiliary component, the main device component comprising:

an image sensor configured to generate image data indicative of a view from the main device component, a light emitter configured to provide illumination of the view, and a main coupling component having one or more main terminals electrically connected to the light emitter and the image sensor, and the auxiliary component comprising:

an auxiliary coupling component configured to removably couple with the main coupling component, the auxiliary coupling component comprising one or more auxiliary terminals configured to connect to the one or more main terminals of the main coupling component, when the auxiliary coupling component is coupled with the main coupling component, a device processor electrically connected to the one or more auxiliary terminals and configured to receive the image data from the image sensor, when the auxiliary component is coupled to the main device component, and encode the image data to provide encoded image data based on the image data, one or more auxiliary communication interfaces including a device wireless transceiver connected to the device processor and configured to communicate with the monitor wireless transceiver of the monitor device, the device wireless transceiver being configured to receive the encoded image data from the device processor and transmit the encoded image data using a downstream data channel to the monitor wireless transceiver of the monitor device, and an auxiliary memory storing initial data, wherein the auxiliary component is configured to transmit the initial data to the monitor device, wherein the monitor processor is configured to receive the initial data and adjust one or more parameters of the medical visualisation system based on the initial data, wherein the monitor device is configured to cause a display to display a live representation of the image data, wherein the initial data comprises operator setup data associated with the operator performing the medical visualisation procedure, wherein the operator setup data includes image parameters including one or more of settings of hue, saturation, brightness, contrast, and sharpness, and wherein the monitor processor is configured to, in response to receiving the initial data, adjust image parameters of the live representation of the image data displayed on the display in accordance with the image parameters of the operator setup data.

18. The medical visualisation system of claim 17, wherein the monitor processor or the device processor is configured to store an image data file in the auxiliary memory in response to receipt of a user input signal indicative of a user activating an image capture button, wherein the image data file corresponds to the image data received when the image capture button was activated.

19. The medical visualisation system of claim 18, wherein the monitor device displays with the display one or more monitor buttons comprising the image capture button, and/or wherein the main device component comprises one or more device buttons comprising the image capture button.

20. A medical visualisation system comprising:

a monitor device including a first housing, one or more monitor communication interfaces including a monitor wireless transceiver, a monitor processor, and a monitor memory; and a first medical visualisation device for performing a medical visualisation procedure, the first medical visualisation device including a main device component and an auxiliary component, the main device component comprising:

an image sensor configured to generate image data indicative of a view from the main device component, a light emitter configured to provide illumination of the view, and a main coupling component having one or more main terminals electrically connected to the light emitter and the image sensor, and the auxiliary component comprising:

an auxiliary coupling component configured to removably couple with the main coupling component, the auxiliary coupling component comprising one or more auxiliary terminals configured to connect to the one or more main terminals of the main coupling component, when the auxiliary coupling component is coupled with the main coupling component, a device processor electrically connected to the one or more auxiliary terminals and configured to receive the image data from the image sensor, when the auxiliary component is coupled to the main device component, and encode the image data to provide encoded image data based on the image data, one or more auxiliary communication interfaces including a device wireless transceiver connected to the device processor and configured to communicate with the monitor wireless transceiver of the monitor device, the device wireless transceiver being configured to receive the encoded image data from the device processor and transmit the encoded image data using a downstream data channel to the monitor wireless transceiver of the monitor device, and an auxiliary memory storing initial data, wherein the auxiliary component is configured to transmit the initial data to the monitor device, wherein the monitor processor is configured to receive the initial data and adjust one or more parameters of the medical visualisation system based on the initial data, wherein the monitor device is configured to cause a display to display a live representation of the image data, wherein the initial data comprises operator setup data associated with the operator performing the medical visualisation procedure, wherein the initial data comprises operator setup data associated with the operator performing the medical visualisation procedure, the monitor device further comprising one or more buttons configured to receive user inputs, and wherein the operator setup data includes button settings indicative of functions assigned to one or more of the buttons, and wherein the monitor processor is configured to, in response to receiving the initial data, assign functions to the one or more of the buttons in accordance with the button settings of the operator setup data.

21. A medical visualisation system comprising:

a monitor device including a first housing, one or more monitor communication interfaces including a monitor wireless transceiver, a monitor processor, and a monitor memory; and a first medical visualisation device for performing a medical visualisation procedure, the first medical visualisation device including a main device component and an auxiliary component, the main device component comprising:

an image sensor configured to generate image data indicative of a view from the main device component, a light emitter configured to provide illumination of the view, and a main coupling component having one or more main terminals electrically connected to the light emitter and the image sensor, and the auxiliary component comprising:

an auxiliary coupling component configured to removably couple with the main coupling component, the auxiliary coupling component comprising one or more auxiliary terminals configured to connect to the one or more main terminals of the main coupling component, when the auxiliary coupling component is coupled with the main coupling component, a device processor electrically connected to the one or more auxiliary terminals and configured to receive the image data from the image sensor, when the auxiliary component is coupled to the main device component, and encode the image data to provide encoded image data based on the image data, one or more auxiliary communication interfaces including a device wireless transceiver connected to the device processor and configured to communicate with the monitor wireless transceiver of the monitor device, the device wireless transceiver being configured to receive the encoded image data from the device processor and transmit the encoded image data using a downstream data channel to the monitor wireless transceiver of the monitor device, and an auxiliary memory storing initial data, wherein the auxiliary component is configured to transmit the initial data to the monitor device, wherein the monitor processor is configured to receive the initial data and adjust one or more parameters of the medical visualisation system based on the initial data, wherein the monitor device is configured to cause a display to display a live representation of the image data, wherein the initial data comprises operator setup data associated with the operator performing the medical visualisation procedure, wherein the monitor processor is configured to perform tasks based on spoken inputs, and the operator setup data includes voice control data associated with the operator performing the medical visualisation procedure, and wherein the monitor processor is configured to, after receiving the initial data, identifies identify tasks to be performed based on the spoken inputs and the voice control data of the initial data.

* * * * *